(12) United States Patent
Bickford

(10) Patent No.: US 8,840,929 B2
(45) Date of Patent: *Sep. 23, 2014

(54) COSMETIC COMPOSITIONS WITH NEAR INFRA-RED (NIR) LIGHT-EMITTING MATERIAL AND METHODS THEREFOR

(71) Applicant: ELC Management LLC, Melville, NY (US)

(72) Inventor: William Robert Bickford, Ronkonkoma, NY (US)

(73) Assignee: ELC Management LLC, Melville, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/095,255

(22) Filed: Dec. 3, 2013

(65) Prior Publication Data

US 2014/0161883 A1 Jun. 12, 2014

Related U.S. Application Data

(60) Provisional application No. 61/735,582, filed on Dec. 11, 2012.

(51) Int. Cl.
| | | |
|---|---|---|
| *A61K 9/14* | (2006.01) | |
| *A61Q 19/08* | (2006.01) | |
| *A61Q 19/00* | (2006.01) | |
| *A61Q 7/00* | (2006.01) | |
| *A61K 8/26* | (2006.01) | |
| *A61K 8/25* | (2006.01) | |
| *A61Q 17/04* | (2006.01) | |
| *A61Q 5/12* | (2006.01) | |
| *A61Q 19/06* | (2006.01) | |
| *A61Q 1/06* | (2006.01) | |
| *A61Q 1/12* | (2006.01) | |
| *A61K 8/27* | (2006.01) | |
| *A61Q 5/06* | (2006.01) | |
| *A61K 8/22* | (2006.01) | |
| *A61Q 3/02* | (2006.01) | |
| *A61Q 9/04* | (2006.01) | |
| *A61Q 1/08* | (2006.01) | |
| *A61K 8/19* | (2006.01) | |
| *A61Q 1/10* | (2006.01) | |
| *A61Q 5/02* | (2006.01) | |

(52) U.S. Cl.
CPC . *A61K 8/27* (2013.01); *A61Q 19/08* (2013.01); *A61Q 19/004* (2013.01); *A61Q 7/00* (2013.01); *A61K 8/26* (2013.01); *A61K 8/25* (2013.01); *A61Q 17/04* (2013.01); *A61Q 5/12* (2013.01); *A61Q 19/06* (2013.01); *A61Q 1/06* (2013.01); *A61Q 1/12* (2013.01); *A61Q 5/06* (2013.01); *A61K 8/22* (2013.01); *A61Q 3/02* (2013.01); *A61Q 9/04* (2013.01); *A61Q 1/08* (2013.01); *A61K 8/19* (2013.01); *A61Q 1/10* (2013.01); *A61Q 19/007* (2013.01); *A61Q 5/02* (2013.01)

USPC .......................................................... 424/489

(58) Field of Classification Search
None
See application file for complete search history.

(56) References Cited

U.S. PATENT DOCUMENTS

| | | |
|---|---|---|
| 3,439,088 A | 4/1969 | Edman |
| 3,781,417 A | 12/1973 | Welters et al. |
| 3,818,105 A | 6/1974 | Coopersmith et al. |
| 4,677,152 A | 6/1987 | Allen et al. |
| 4,702,844 A | 10/1987 | Flesher et al. |
| 4,803,067 A | 2/1989 | Brunetta et al. |
| 4,970,252 A | 11/1990 | Sakuta et al. |
| 5,077,211 A | 12/1991 | Yarosh |
| 5,118,496 A | 6/1992 | Herstein |
| 5,183,588 A | 2/1993 | Salerno et al. |
| 5,183,589 A | 2/1993 | Brunetta et al. |
| 5,190,762 A | 3/1993 | Yarosh |
| 5,236,986 A | 8/1993 | Sakuta |
| 5,272,079 A | 12/1993 | Yarosh |
| 5,296,231 A | 3/1994 | Yarosh |
| 5,412,004 A | 5/1995 | Tachibana et al. |
| 5,654,362 A | 8/1997 | Schulz, Jr. et al. |
| 5,760,116 A | 6/1998 | Kilgour et al. |
| 5,811,487 A | 9/1998 | Schulz, Jr. et al. |
| 5,837,793 A | 11/1998 | Harashima et al. |
| 5,843,193 A | 12/1998 | Hawkins et al. |
| 6,311,359 B1 | 11/2001 | Brezler, III |
| 6,313,181 B1 * | 11/2001 | Cohen ............................ 424/59 |
| 6,592,882 B2 | 7/2003 | George et al. |
| 6,753,002 B2 * | 6/2004 | George et al. ................. 424/401 |
| 2003/0091602 A1 | 5/2003 | Witteler et al. |
| 2004/0166146 A1 | 8/2004 | Holloway et al. |

(Continued)

FOREIGN PATENT DOCUMENTS

| | | |
|---|---|---|
| JP | 61-18708 | 1/1986 |
| JP | 11-178899 | 7/1999 |
| KR | 20100037494 | 4/2010 |
| WO | WO 0200190 A1 * | 1/2002 |
| WO | WO-03/015661 | 2/2003 |
| WO | WO-2004/024798 | 3/2004 |
| WO | WO-2010/096733 | 8/2010 |
| WO | WO-2011/063356 | 5/2011 |
| WO | WO-2012/107550 | 8/2012 |

OTHER PUBLICATIONS

Escribano et al. Photonic and nanobiophotonic properties of luminescent lanthanide-doped hybrid organic-inorganic materials. J. Mater. Chem., 2008, 18:23-40.*

(Continued)

*Primary Examiner* — Robert A Wax
*Assistant Examiner* — Olga V Tcherkasskaya
(74) *Attorney, Agent, or Firm* — Cynthia R. Miller

(57) ABSTRACT

Cosmetic or dermatological compositions and substrates, containing a NIR light-emitting material, and methods for stimulating healing and/or regenerative properties in the skin, hair and/or scalp are provided.

12 Claims, 4 Drawing Sheets

(56) References Cited

U.S. PATENT DOCUMENTS

| | | |
|---|---|---|
| 2004/0193236 A1 | 9/2004 | Altshuler et al. |
| 2006/0174436 A1 | 8/2006 | Brezler |
| 2007/0071978 A1* | 3/2007 | Sojka et al. ............... 428/402.2 |
| 2007/0172439 A1 | 7/2007 | Tamura et al. |
| 2008/0073594 A1 | 3/2008 | Lee |
| 2011/0288234 A1* | 11/2011 | Pandey et al. ............... 525/54.1 |
| 2011/0293529 A1* | 12/2011 | Ji et al. ............... 424/9.6 |
| 2012/0060858 A1 | 3/2012 | Bickford et al. |
| 2012/0093935 A1* | 4/2012 | Dembski et al. ............... 424/490 |

OTHER PUBLICATIONS

Chermont et al., Nanoprobes with near-infrared persistent luminescence for in vivo imaging. PNAS 2007, 100(22):9266-9271.*

Pan, et al.; Sunlight-activated long-persistent luminescence in the near-infrared from $Cr^{3+}$-doped zinc gallogermanates; Nature materials; vol. 11; pp. 58-63; www.nature.com/naturematerials; Jan. 2012.

PCT International Search Report; International Application No. PCT/US2013/072975; Completion Date: Mar. 17, 2014; Date of Mailing: Mar. 17, 2014.

PCT International Search Report; International Application No. PCT/US2013/072985; Completion Date: Mar. 18, 2014; Date of Mailing: Mar. 18, 2014.

PCT International Search Report; International Application No. PCT/US2013/072990; Completion Date: Mar. 17, 2014; Date of Mailing: Mar. 17, 2014.

PCT International Search Report; International Application No. PCT/US2013/072994; Completion Date: Mar. 18, 2014; Date of Mailing: Mar. 18, 2014.

PCT Written Opinion of the International Searching Authority; International Application No. PCT/US2013/072975; Completion Date: Mar. 17, 2014; Mailing Date: Mar. 17, 2014.

PCT Written Opinion of the International Searching Authority; International Application No. PCT/US2013/072985; Completion Date: Mar. 18, 2014; Mailing Date: Mar. 18, 2014.

PCT Written Opinion of the International Searching Authority; International Application No. PCT/US2013/072990; Completion Date: Mar. 17, 2014; Mailing Date: Mar. 17, 2014.

PCT Written Opinion of the International Searching Authority; International Application No. PCT/US2013/072994; Completion Date: Mar. 18, 2014; Mailing Date: Mar. 18, 2014.

PCT International Search Report; International Application No. PCT/US2013/073007; Completion Date: Jun. 24, 2014; Date of Mailing: Jun. 25, 2014.

PCT Written Opinion of the International Searching Authority; International Application No. PCT/US2013/073007; Completion Date: Jun. 24, 2014; Mailing Date: Jun. 25, 2014.

* cited by examiner

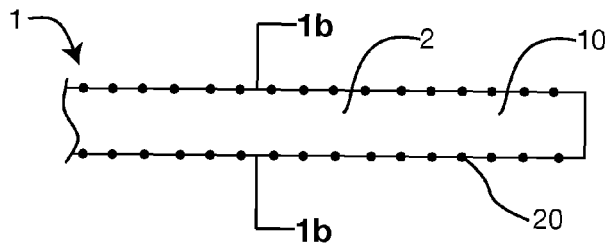
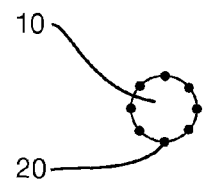
FIG. 1a  FIG. 1b
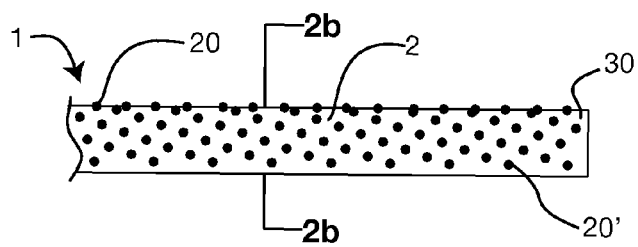
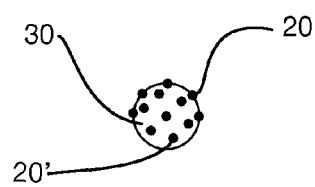
FIG. 2a  FIG. 2b
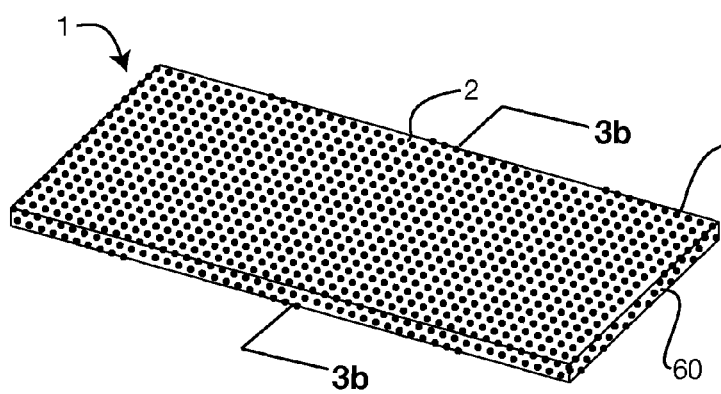
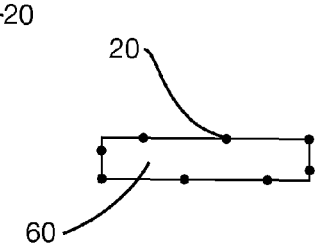
FIG. 3a  FIG. 3b
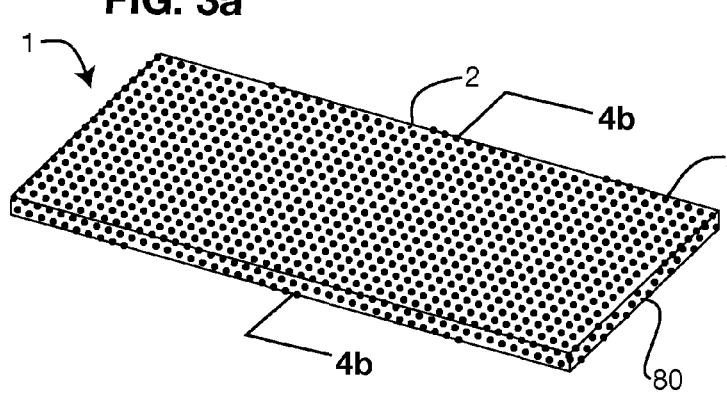
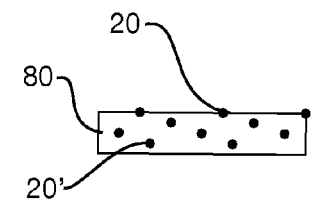
FIG. 4a  FIG. 4b

COSMETIC COMPOSITIONS WITH NEAR INFRA-RED (NIR) LIGHT-EMITTING MATERIAL AND METHODS THEREFOR

CROSS-REFERENCE TO RELATED APPLICATIONS

The present application claims priority from U.S. Provisional Application No. 61/735,582, filed Dec. 11, 2012.

BACKGROUND OF THE INVENTION

1. Field of the Invention

The present invention relates to cosmetic formulations with long-term benefits. More specifically, the present invention is directed to cosmetic products for the body, and in particular, for the skin, scalp and/or hair, which incorporate a material which emits near-infra-red (NIR) light.

2. Description of the Prior Art

Just about everyone would like to maintain an ageless, youthful appearance. Consumers are always looking for the next product or treatment that will erase their wrinkles and keep them younger looking, and in particular, safer and more effective methods and products for rejuvenating the skin. Collagen and elastin are the components of skin which keep it young looking. Collagen molecules pack together to form long thin fibrils, and, together with elastin, form bundles which serve to make skin layers elastic and therefore help the skin to withstand stretching. But these components decrease as people age. Moreover, sun exposure, smoking and environmental stresses alter and degrade the skin's collagen and elastin. Sun exposure, in particular, induces matrix metalloproteinases (MMPs), a group of enzymes, to degrade and disorganize collagen bundles, likely contributing to wrinkle formation. Various methods, including hyaluronic acid injections, topical application of Vitamin C compounds or Vitamin A compounds (e.g., retinoids), have been used to boost or prevent the loss of collagen. Other methods, including dermabrasion, chemical skin peels, electrical stimulation, Collagen Induction therapy (CIT) utilizing a micro-needle studded roller, dermal fillers, laser treatments, and the like, are said to improve the appearance of skin by agitating skin and triggering healing and/or stimulating neocollagenesis. However, aggressive methods, particularly dermabrasion and chemical peels, have been observed to be destructive to skin and further have the potential for long-term side-effects including redness and scarring. Moreover, all of these treatments are costly procedures, and may only be performed by a professional.

It has recently been reported that photobiomodulation, also known as low level laser therapy (LLLT), leads to beneficial clinical effects, including wound healing. This is a technique in which exposure to low-energy lasers or LED (light emitting diode) arrays stimulates cellular function. It has been observed that, in cells damaged by injury or trauma, energy producing mitochondria are turned off so that the production of energy in the form of ATP is reduced or ceases entirely. When these cells are exposed to infra-red or near infra-red light, by means of LLLT, at the right frequency, the mitochondria are re-activated and almost immediately begin producing adenosine 5' diphosphate (ADP) which links with free oxygen singlets to produce adenosine 5' triphosphate (ATP), the energy source for metabolic processes in cells. More specifically, it is believed that the mechanism of photobiomodulation at the cellular level involves the activation of mitochondrial respiratory chain components, resulting in a signaling cascade initiated by the absorption of light by cytochrome oxidase, an integral membrane protein that has a strong absorbency in the far-red to near infra-red spectral range, promoting cellular proliferation and cytoprotection. The effectiveness of this therapy appears to be related to the color of the laser light (wavelength), the intensity, and the total energy delivered. The correct dose of laser irradiation is said to effect improvements in the rate and quality of not only wound healing, but also pain relief, inflammation, immune system functioning and nerve regeneration.

It has further been observed that LLLT therapy stimulates neocollagenesis, tightens collagen fibers, and stimulates the production of elastin, all of which are said to be beneficial for improving the appearance of skin texture or topography, including reducing the appearance of dilated pores and wrinkles, while being minimally invasive. Additionally, LED devices have been used to apply NIR light to the scalp to stimulate healing and the growth phase of hair follicles that have become dormant, as well as to reduce dandruff-causing seborrhoeic inflammation. It has also been reported that LLLT therapy stimulates cell growth, both directly, by regulating the expression of certain genes, and indirectly, by regulating the expression of genes related to DNA synthesis and repair, and cell metabolism. Others studies have suggested that LLLT therapy is useful in reducing the appearance of cellulite. LLLT therapy in combination with moderate exercise has also been reported to play a role in fat reduction and weight loss. The results of the study indicated that NIR light acts by thermal and non-thermal mechanisms. The thermal effects include the generation of a therapeutic field of warmth with an increase in tissue temperature, tissue oxygen partial pressure, and tissue blood flow. The NIR light boosts the normally slow metabolism and rate of lipolysis of the tissue, and the mobilized fats are burned in musculature during the exercise.

It is the Applicants' understanding that NIR light-emitting material has not heretofore been incorporated into a topical cosmetic product so as to provide the benefits previously achieved only with NIR light-emitting devices such as lasers. It would be advantageous to provide methods and products to consumers for achieving skin and hair therapy or rejuvenation which do not require the use of devices such as lasers or LEDs or a dermatologist to apply the therapy.

SUMMARY OF THE INVENTION

It is an object of the present invention to provide cosmetic or dermatological compositions comprising a NIR light-emitting material in a cosmetically or dermatologically acceptable vehicle.

It is also an object of the present invention to provide cosmetic or dermatological compositions comprising a NIR light-emitting material which persistently emits NIR light in a cosmetically or dermatologically acceptable vehicle.

It is a further object of the present invention to provide cosmetic or dermatological compositions comprising a NIR light-emitting material in combination with at least one skin, scalp, hair and/or body benefit agent in a cosmetically or dermatologically acceptable vehicle.

It is another object of the present invention to provide cosmetic or dermatological compositions for stimulating healing or regenerative properties in the skin, scalp and/or hair comprising a NIR light-emitting material, in a cosmetically or dermatologically acceptable vehicle.

It is also an object of the present invention to provide cosmetic or dermatological compositions for stimulating healing or regenerative properties in the skin, scalp and/or hair comprising a NIR light-emitting material in combination with at least one skin, scalp and/or hair benefit agent, in a cosmetically or dermatologically acceptable vehicle.

It is another object of the present invention to provide a substrate for stimulating healing or regenerative properties in the skin, scalp and/or hair, the substrate comprising
   a solid body; and
   a NIR light-emitting material associated with the solid body.

It is yet a further object of the present invention to provide a method for stimulating a healing or regenerative property in the skin, scalp and/or hair comprising:
   applying to the skin, scalp and/or hair in need of such treatment a cosmetic or dermatological composition comprising a NIR light-emitting material, in a cosmetically or dermatologically acceptable vehicle; and
   retaining the composition in contact with the skin, scalp and/or hair for a time sufficient to stimulate a healing or regenerative property in the skin, scalp and/or hair, wherein the composition is exposed to UV or fluorescent light prior to, during, or after application of the composition to the skin, scalp and/or hair for a time sufficient to activate the NIR light-emitting material.

It is another object of the present invention to provide a method for stimulating healing or regenerative properties in the skin, scalp and/or hair comprising:
   applying to the skin or hair in need of such treatment a cosmetic or dermatological composition comprising a NIR light-emitting material in combination with at least one skin, scalp and/or hair benefit agent, in a cosmetically or dermatologically acceptable vehicle; and
   retaining the composition in contact with the skin, scalp and/or hair for a time sufficient to stimulate a healing or regenerative property to the skin, scalp and/or hair, wherein the composition is exposed to UV or fluorescent light prior to, during, or after application of the composition to the skin, scalp and/or hair for a time sufficient to activate the NIR light-emitting material.

It is a further object of the present invention to provide a method for improving body composition, comprising:
   applying to skin of at least one body part containing fatty tissue and in need of such improvement, a cosmetic or dermatological composition comprising a NIR light-emitting material, which is capable of providing thermal effects on fatty tissue, in a cosmetically or dermatologically acceptable vehicle: and
   retaining the composition in contact with the skin of the at least one body part, while exercising the at least one body part, for a time sufficient to generate the thermal effects of the NIR light on the fatty tissue to thereby increase lipolysis in the fatty tissue and boost fat reduction in the body part; wherein the composition is exposed to UV or fluorescent light prior to, during or after application of the composition to the skin of the at least one body part for a time sufficient to activate the NIR light-emitting material.

Other aspects and objectives of the present invention will become more apparent from the ensuing description and claims.

BRIEF DESCRIPTION OF THE DRAWINGS

FIG. 1a is an elevational view of a fiber or bristle incorporating NIR light-emitting particles on its surface;

FIG. 1b is a cross-sectional of the fiber or bristle of FIG. 1a, taken along line 1b-1b;

FIG. 2a is an elevational view of a fiber or bristle incorporating embedded NIR light-emitting particles throughout and NIR light-emitting particles on a portion of the surface of the fiber;

FIG. 2b is cross-sectional view of the fiber or bristle of FIG. 2a, taken along line 2b-2b;

FIG. 3a is a top, perspective view of a sheet incorporating NIR light-emitting particles on its surface;

FIG. 3b is a cross-sectional view of the sheet of FIG. 3a, taken along line 3b-3b;

FIG. 4a is a top, perspective view of a sheet incorporating embedded NIR light-emitting particles throughout and NIR light-emitting particles on a portion of the surface of the sheet;

FIG. 4b is a cross-sectional view of the sheet of FIG. 4a, taken along line 4b-4b;

DETAILED DESCRIPTION OF THE PREFERRED EMBODIMENTS OF THE INVENTION

Figure 5:
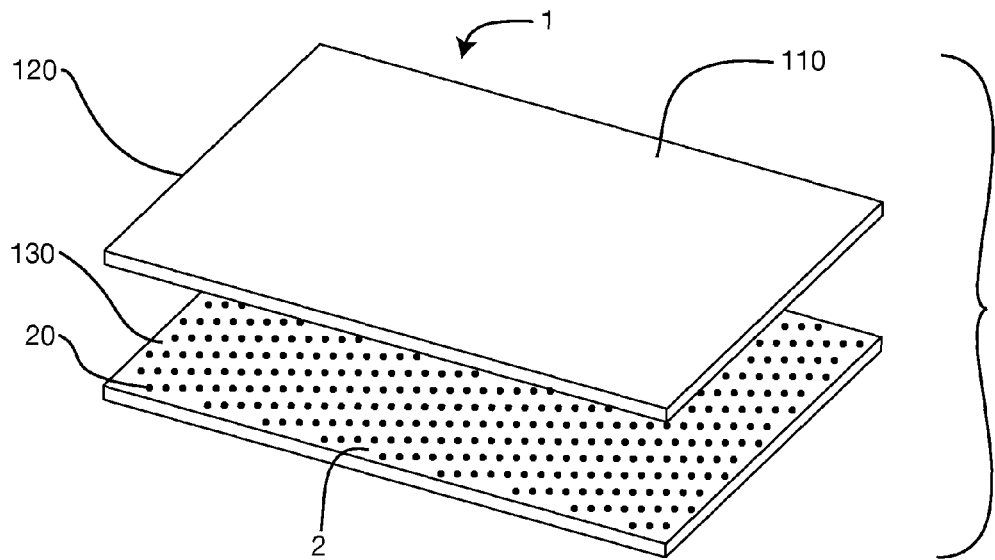
FIG. 5 is an exploded top, perspective view of a multi-layered sheet, the upper surface of the lower sheet incorporating NIR light-emitting particles.

Long persistent-phosphorescence phenomena are well-known. Long-persistent phosphors in the visible region have been well-developed and widely applied in such various fields as security signs, emergency route signs, safety indication, and indicators of control panels in dark environments or in the night. Additionally, materials which emit visible light after exposure to sunlight are well-known, e.g., glow-in-the-dark stickers, toys, and the like. It is also known to use luminescent materials e.g., ZnS:Cu phosphor, in glow in the dark cosmetics, such as lipstick. These products glow in the dark when exposed to ultraviolet (UV) irradiation. In contrast, research and development of long-persistent phosphors in the NIR regions (650-900 nm wavelengths), the region of the light spectrum closest in wavelength to the radiation detectable by the human eye, have progressed more slowly compared with their visible counterparts. NIR is most commonly known for use in fiber optic telecommunications and in night vision devices such as goggles when there is insufficient light to see. Such devices operate by converting ambient visible light photons into electrons which are then amplified by a chemical and electrical process and converted back into visible light. NIR-persistent phosphors with afterglow are also known. These phosphors require sunlight (UV light) for excitation and demonstrate emission periods of a few minutes to a few hours.

Surprisingly, to the Applicants' knowledge, to date, there are no cosmetic formulations which incorporate a NIR light-emitting material and which can provide the benefits to the body, and in particular, to the skin, scalp and/or the hair, previously observed only with the use of devices. Nevertheless, as exposure to sunlight is associated with harmful effects (i.e., burning; premature aging, including skin wrinkling; skin cancer; etc.) on the skin and even the hair, it would be desirable to incorporate into cosmetic and/or dermatological products, NIR light-emitting materials which do not require extended periods of exposure to UV light for excitation. Additionally, it would be appreciated by users of such products if the NIR light emission period would last for a longer period of time than that time provided by exposure to a laser or LED device, and more preferably, for more than a few hours. Furthermore, products which do not require a device or instrument, such as a laser, to administer, would be greatly appreciated by consumers. The present invention is therefore concerned with providing cosmetic products and methods which incorporate a NIR light-emitting material which requires only minimal exposure to UV light for excitation and which demonstrates a long-lasting emission period; that is, persistent, long-term effects in contrast with those effects obtainable from discrete or isolated treatments provided by devices emitting NIR light. Additionally, the benefits of the present invention may be achieved without costly office visits to a trained professional.

In accordance with one aspect of the present invention, cosmetic or dermatological compositions which incorporate a material which emits NIR light in a cosmetically or dermatologically acceptable vehicle are provided.

Therapeutic benefits obtainable with compositions of the present invention include any of the benefits obtainable with the use of LLLT therapy, including, but not limited to, stimulation of collagen and/or elastin production in skin; improvement in the texture of skin, such as by reducing the size of pores in the skin, reducing the size and/or depth of wrinkles in the skin, reduction in the appearance of cellulite in the skin; reduction in inflammation in the skin; evening the skin tone; treatment of acne; reduction in the appearance of acne scarring on the skin; enhancement of DNA synthesis and repair; rejuvenation of the hair and scalp, such as by stimulation of the growth phase of hair follicles, including dormant hair follicles, smoothing of the hair cuticle, and reduction in seborrhoiec inflammation.

Any material which emits NIR light, and which is not toxic for use on the human body, including the skin, scalp and/or hair, may be used in the compositions of the present invention. Useful NIR light-emitting materials may include, but are not limited to, inorganic luminescent materials of the type widely used for applications such as emergency guiding signs, luminous paints, and in vivo diagnostic imaging, such as, but not limited to, phosphors of $MgSiO_3:Eu^{2+}$ $Dy^{3+}$, $Mn^{2+}$; $Ca_{0.2}Zn_{0.9}Mg_{0.9}Si_2O_6$, doped with $Eu^{2+}$, $Dy^+$, $Mn^{2+}$; $SrAl_2O_4$: $Eu^{2+}$, $Dy^{3+}$, $Er^{3+}$; $La_3Ga_5Ge_3O_{14}:Cr^{3+}$, with or without co-dopants such as $Li^+$, $Zn^{2+}$, $Ca^{2+}$, $Mg^{2+}$ and $Dy^{3+}$; $Ln_3Ga_2Ge_4O_{14}:Cr^{3+}$ (Ln=Y, Gd, La or Lu); $LiGa_5O_8:Cr^{3+}$; $M_3Ga_2Ge_4O_{14}:Cr^{3+}$ (M=Sr or Ca); $La_3Ga_5SiO_{14}:Cr^{3+}$; $La_3Ga_{5.5}Nb^{0.5}O_{14}:Cr^{3+}$; $La_3Ga_5GeO_{14}:Cr^{3+}$; $Gd_3Ga_5O12$:$Cr^{3+}$; $Zn_3Ga_2Ge_2O_{10}$:0.5% $Cr^{3+}$; and ceramic-metallo composites, for example, those comprising boron powder, such as used in hairstyling irons; and the like.

The NIR light-emitting material may also comprise organic luminescent materials, such as those typically used as probes in diagnostic imaging processes, for example, near infra-red fluorescence (NIRF) probes bound to natural or synthetic polymers, peptides, glucose analogs, fluorescent gold nanoclusters entrapped in bovine serum albumin and silica; and so forth. Additionally, since heme-related molecules, such as porphyrin- (heme-) containing proteins, i.e., cytochromes, found in mitochondria, are reported to be receivers and emitters of NIR light, these natural molecules, as well as heme-containing chlorophylls, Pt-porphyrin ring systems, and the like, are contemplated for use in the compositions and methods of the present invention. It is contemplated that the use of two or more different NIR light-emitting materials may have an amplifying or synergistic effect rather than merely an additive effect provided by the individual materials.

NIR light-emitting materials useful in the compositions of the invention are activated by absorbing UV or fluorescent light during brief exposure periods of, for example, from about 1 minute to about 10 minutes. Preferably, the NIR light-emitting materials emit a long-lasting, near infra-red glow after only minimal exposure to UV light. By "long-lasting", it is meant that the NIR light-emission period is at least about 1 hour to several weeks, such as about 6 weeks, including all time periods in-between, such as from at least about 8 hours to about 2 weeks, after only an initial brief exposure to UV or fluorescent light. More preferably, the NIR light-emission period is at least about 24 hours to about 1 week. However, it will be appreciated that the NIR light-emitting materials in the compositions of the present invention, once applied to the body, may be continually reactivated or recharged by exposure to UV or fluorescent light over an extended period of time while the compositions remain in contact with the body.

In one preferred embodiment of this aspect of the present invention, the cosmetic or dermatological compositions comprise a NIR light-emitting material which absorbs and emits a near infra-red glow for up to about 2 weeks after minimal exposure to UV light. Such "persistent" NIR light-emitting materials contain the trivalent chromium ion, a recognized emitter of NIR light. When exposed to UV light, the trivalent chromium ion's electrons at ground state rapidly move to a higher energy state. As the electrons return to the ground state, energy is released as NIR light. The period of light emission from the trivalent chromium ion, however, is relatively short (i.e., a few milliseconds). The luminescence of the long-persistent luminescent material, based on the chromium ion, lasts for many hours after the excitation has ceased. The long-persistent luminescent material contains two kinds of active centers, emitters and traps. The emitters emit radiation after being excited. The traps do not emit radiation but store excitation energy and release it gradually to the emitters. One class of such long-persistent luminescent material employs chromium-doped zinc gallogermanate NIR persistent phosphors in which a matrix of zinc and gallogermanate ("traps") hosts the trivalent chromium ions ("emitters). The general chemical formula for these phosphors can be written as $Zn_x Ga_y Ge_z O_{(x+(3y/2)+2z)}:tCr^{3+}$, mR where R is a co-dopant selected from a group consisting of alkaline earth ions, lanthanide ions and Li+ ions; x, y and z are integers from 1 to 5; t is 0.01 to 5 mol %; and m is 0 to 5 mol %. One example of the material can be represented by the formula $Zn_3Ga_2Ge_2O_{10}$:0.5% $Cr^{3+}$. These materials are activated by exposure to UV or fluorescent light for a brief time period of only about one minute. As the stored energy is released back to the chromium ions at room temperature, the compound persistently emits NIR light over a period of up to about two weeks. The material may be made in the form of, for example, ceramic discs or micro-powders, such as powders having a particle size of 2-5μ. The powder form may be incorporated into various cosmetic and/or dermatological products which can endow the products with the ability to emit persistent NIR light or afterglow after excitation.

A further aspect of the present invention concerns cosmetic or dermatological compositions comprising an NIR light-emitting material in combination with at least one skin, scalp and/or hair benefit or agent, in a cosmetically or dermatologically acceptable vehicle.

The NIR light-emitting materials employed may be any of the NIR light-emitting materials mentioned hereinabove.

Skin, scalp and hair benefit agents useful in the compositions of the present invention include any such cosmetic or dermatological therapeutic ingredient which results in a benefit to the skin, scalp or hair. While the therapeutic or benefit agents are not particularly limited, preferred are those ingredients which stimulate the production of collagen and/or elastin in skin; improve the texture of skin such as by reducing the size of pores in the skin, reducing the size and/or depth of wrinkles in the skin, reducing the appearance of cellulite in the skin; reduce inflammation in the skin; even the skin tone; treat acne; reduce the appearance of acne scarring on the skin; stimulate DNA synthesis and repair; or which rejuvenate the hair or scalp, such as by stimulating the growth phase of hair follicles, including dormant hair follicles, reducing seborrhoiec inflammation, and so forth, as described in more detail hereinbelow.

Ingredients which stimulate neocollagenesis include, but are not limited to, Vitamin C and its derivatives, for example, tetrahexyldecyl ascorbate; retinoids, Epidermal Growth Factor (EGF), and soybean extracts. Ingredients which stimulate the production of elastin include, but are not limited to, Vitamin C and alguronic acid. Such ingredients have been reported to improve skin texture, reduce the size of pores, reduce the size and/or depth of wrinkles, and reduce the appearance of cellulite.

Other ingredients which have been observed to improve skin texture include, but are not limited to, peptides, such as argeriline (acetyl hexapeptide-3), Matryxil (palmitoyl tetrapeptide-7 and palmitoyl oligopeptide), snake peptide and copper peptides; alpha hydroxy acids, such as glycolic acids; beta hydroxy acids, such as salicylic acids; co-enzyme Q10 (ubiquinone); ceramides; and Vitamin A. Further agents which are said to improve the appearance of cellulite include methylxanthines (e.g., caffeine, aminophylline and theophylline) which are also indicated in promoting lipolysis; and green tea extracts, e.g., EGCG.

Ingredients which reduce inflammation in the skin include, but are not limited to, niacinamide, quercetin, salicylic acid, alpha bisabolol, EGF, coffeeberry extract and dipotassium glycyrrhizinate.

Anti-acne agents include, but are not limited to, benzoyl peroxide, salicylic acid, willow bark extract, niacinamide, epigallocatechin gallate (EGCG), zinc, yeast beta glucans, saw palmetto extract, retinoids, nobiletin, ascorbyl tetraisopalmitate, dipotassium glycyrrhizinate, alpha bisabolol, sulfur and quercetin.

Ingredients which reduce the appearance of acne scarring on the skin include, but are not limited to, bleaching ingredients such as hydroquinone, and its derivatives, for example, arbutin; kojic acid; azelaic acid; Vitamins C and E; alpha hydroxy acids; niacinamide; licorice extract, pomegranate extract, ellagic acid; and ferulic acid.

Scalp-, and particularly, hair follicle-stimulating ingredients include, but are not limited to, Minoxidil (6-piperidin-1-ylpyrimidine-2,4-diamine 3-oxide); cinnamon bark oil; Vitamin B5; capsaicin; and peppermint (*Mentha piperita*). Anti-dandruff actives include, but are not limited to, Aloe Vera, coconut oil, tea tree oil, oregano oil, *Viola tricolor*, honey, avocado extracts, *Monardo fistulosa* (Wild bergamot), *Lactobacillus casei*, and *Lactobacillus paracasei*, Lactoferrin, Vitamin $B_7$ (Biotin), Vitamin $B_6$, Vitamin $B_2$, Vitamin $B_3$ (Nicotinamide or Niacinamide), Zinc, Blackcurrant seed oil, Milk of Magnesia, and *Boswellia serrata* extracts.

Therapeutic ingredients which stimulate DNA synthesis and repair include, but are not limited to, those DNA repair enzymes disclosed in U.S. Pat. Nos. 5,077,211; 5,190,762; 5,272,079; and 5,296,231, each of which is hereby incorporated by reference in its entirety. One example of such a DNA repair enzyme may be purchased from AGI Dermatics under the trade name Roxisomes®, and has the INCI name *Arabidopsis Thaliana* extract. It may be present alone or in admixture with lecithin and water. This DNA repair enzyme is known to be effective in repairing 8-oxo-diGuanine base mutation damage.

Another type of DNA repair enzyme that may be used is one that is known to be effective in repairing O-6-methyl guanine base mutation damage. It is sold by AGI Dermatics under the trade name Adasomes®, and has the INCI name *Lactobacillus* ferment, which may be added to the composition of the invention by itself or in admixture with lecithin and water.

Another type of DNA repair enzyme that may be used is one that is known to be effective in repairing T-T dimers. The enzymes are present in mixtures of biological or botanical materials. Examples of such ingredients are sold by AGI Dermatics under the trade names Ultrasomes® or Photosomes®. Ultrasomes® comprises a mixture of *Micrococcus* lysate (an end product of the controlled lysis of a species of *micrococcus*), lecithin, and water. Photosomes® comprises a mixture of plankton extract (which is the extract of a biomass which includes enzymes from one or more of the following organisms: thalassoplankton, green micro-algae, diatoms, greenish-blue and nitrogen-fixing seaweed), water, and lecithin.

Another type of DNA repair enzyme may be a component of various inactivated bacterial lysates such as Bifida lysate or Bifida ferment lysate, the latter a lysate from Bifido bacteria which contains the metabolic products and cytoplasmic fractions when Bifido bacteria are cultured, inactivated and then disintegrated. This material has the INCI name Bifida Ferment Lysate.

Other suitable DNA repair enzymes include Endonuclease V, which may be produced by the denV gene of the bacteriophage T4. Also suitable are T4 endonuclease; O-6-methylguanine-DNA methyltransferases; photolyases, base glycosylases such as uracil- and hypoxanthine-DNA glycosylases; apyrimidinic/apurinic endonucleases; DNA exonucleases, damaged-bases glycosylases (e.g., 3-methyladenine-DNA glycosylase); correndonucleases either alone or in complexes (e.g., *E. coli* uvrA/uvrB/uvrC endonuclease complex); APEX nuclease, which is a multi-functional DNA repair enzyme often referred to as "APE"; dihydrofolate reductase; terminal transferase; polymerases; ligases; and topoisomerases.

Other types of suitable DNA repair enzymes may be categorized by the type of repair facilitated and include BER (base excision repair) or BER factor enzymes such as uracil-DNA glycosylase (UNG); single strand selective monofunctional uracil DNA glycosylase (SMUG1); 3,N(4)-ethenocytosine glycosylase (MBD4); thymine DNA-glycosylase (TDG); A/G-specific adenine DNA glycosylase (MUTYH); 8-oxoguanine DNA glycosylase (OGG1); endonuclease III-like (NTHL1); 3-methyladenine DNA glycosidase (MPG); DNA glycosylase/AP lyase (NEIL1 or 2); AP endonuclease (APEX 1 and 2), DNA ligase (LIG3), ligase accessory factor (XRCC1); DNA 5'-kinase/3'-phosphatase (PNKP); ADP-ribosyltransferase (PARP1 or 2).

Another category of DNA repair enzymes includes those that are believed to directly reverse damage such as O-6-MeG alkyl transferase (MGMT); 1-meA dioxygenase (ALKBH2 or ALKBH3).

Yet another category of enzymes operable to repair DNA/protein crosslinks includes Tyr-DNA phosphodiesterase (TDP1).

Also suitable are MMR (mismatch excision repair) DNA repair enzymes such as MutS protein homolog (MSH2); mismatch repair protein (MSH3); mutS homolog 4 (MSH4); MutS homolog 5 (MSH5); or G/T mismatch-binding protein (MSH6); DNA mismatch repair protein (PMS1, PMS2, MLH1, MLH3); Postmeiotic segregation increased 2-like protein (PMS2L3); or postmeiotic segregation increased 2-like 4 pseudogene (PMS2L4).

Also suitable are DNA repair enzymes those known as nucleotide excision repair (NER) enzymes and include those such as Xeroderma Pigmentosum group C-complementing protein (XPC); RAD23 (*S. cerevisiae*) homolog (RAD23B); caltractin isoform (CETN2); RFA Protein 1, 2, of 3 (RPA1, 2, or 3); 3' to 5' DNA helicase (ERCC3); 5' to 3' DNA helicase (ERCC2); basic transcription factor (GTF2H1, GTF2H2, GTF2H3, GTF2H4, GTF2H5); CDK activating kinase (CDK7, CCNH); cyclin G1-interacting protein (MNAT1); DNA excision repair protein ERCC-1 or RAD-51; excision repair cross-complementing 1 (ERCC1); DNA ligase 1 (LIG1); ATP-dependent helicase (ERCC6); and the like.

Also suitable may be DNA repair enzymes in the category that facilitate homologous recombination and include, but are not limited to DNA repair protein RAD51 homolog (RAD51, RAD51L1, RAD51B etc.); DNA repair protein XRCC2; DNA repair protein XRCC3; DNA repair protein RAD52; ATPase (RAD50); 3' exonuclease (MRE11A); and so on.

DNA repair enzymes that are DNA polymerases are also suitable and include DNA polymerase beta subunit (POLB); DNA polymerase gamma (POLG); DNA polymerase subunit delta (POLD1); DNA polymerase II subunit A (POLE); DNA polymerase delta auxiliary protein (PCNA); DNA polymerase zeta (POLZ); MAD2 homolog (REV7); DNA polymerase eta (POLH): DNA polymerase kappa (POLK): and the like.

Various types of DNA repair enzymes that are often referred to as "editing and processing nucleases" include 3'-nuclease; 3'-exonuclease; 5'-exonuclease; endonuclease; and the like.

Other examples of DNA repair enzymes include DNA helicases, such as ATP DNA helicase, and so forth.

The DNA repair enzymes may be present as components of botanical extracts, bacterial lysates, biological materials, and the like. For example, botanical extracts may contain DNA repair enzymes.

In accordance with a further aspect of the present invention, cosmetic or dermatological compositions which stimulate healing or regenerative/rejuvenative properties in the skin, scalp and/or hair are provided. These compositions incorporate a material which emits NIR light, in a cosmetically or dermatologically acceptable vehicle.

The NIR light-emitting materials employed may be any of the NIR light-emitting materials mentioned hereinabove.

Healing, regenerative, and/or rejuvenative properties include, but are not limited to, anti-aging treatments, such as stimulating the production of collagen in skin, stimulating the production of elastin in skin, resurfacing the skin, such as by improving the texture of skin, reducing the size of pores in the skin, reducing the size and/or depth of wrinkles in the skin, and reducing the appearance of cellulite in the skin; stimulation of DNA synthesis and repair, reduction of inflammation in the skin; evening skin tone; treatment of acne; reduction in the appearance of acne scarring on the skin; stimulation of DNA synthesis and repair; and rejuvenation of the hair and/or scalp, including stimulation of the growth phase of hair follicles, including dormant follicles, and reducing seborrhoiec inflammation.

According to a preferred embodiment of this aspect of the present invention, cosmetic or dermatological compositions which stimulate healing or regenerative properties in the skin, scalp and/or hair contain the NIR light-emitting material in combination with at least one skin, scalp and/or hair benefit ingredient.

The NIR light-emitting material and the skin, scalp and/or hair benefit ingredients may be any of those mentioned hereinabove.

Skin, scalp and/or hair benefit ingredients are those described hereinabove. Particularly preferred skin benefit agents are those which stimulate neocollagenesis or the production of elastin.

Cosmetic and/or dermatological compositions of the present invention may be found in a variety of forms, such as anhydrous compositions containing organic solvents, such as oils or alcohols; or in hydrous forms, including aqueous-based solutions, serums, gels, creams, lotions, toners, mousses, sprays, ointments, essences, pastes; or in solid forms, such as sticks, microcapsules; any cosmetic product for the hand, face, lip, hair or body, including color cosmetic compositions, such as foundation, blush, eyeshadow, concealer, lipgloss, lip balm, lipstick, mascara and the like; as well as in hair care products, including shampoo, conditioner, masks, serums, styling lotions and balms; sun care products, depilatories, exfoliants, and so forth. The NIR-emitting material may be dispersed in either the aqueous phase or the non-aqueous phase of the composition.

The NIR light-emitting material may be present in the compositions of the invention in amounts in the range of from about 0.001 wt. % to about 99.99 wt. %, including any amounts in-between those amounts, such as in the range of from about 0.01 wt. % to about 75 wt. %, for example, from about 0.1 wt. % to about 30 wt. %, or for another example, from about 0.1 wt. % to about 5 wt. %. The particle size of the NIR light-emitting material may be in the range of from about 100 nanometers to about 100 micrometers, including any amounts in-between those amounts, for example, from about 500 nanometers to about 20 micrometers. Preferably, the particle size is in the range of from about 250 nanometers to about 10 micrometers, such as from about 1 micrometer to about 5 micrometers.

Although the NIR light-emitting material useful in the compositions of the invention may be used in particle form, it will be understood that the material may also be encapsulated or entrapped in any delivery system known for use with cosmetic and/or dermatological ingredients, including, but not limited to vesicles; microspheres, such as hollow microspheres; liposomes; and so forth.

As examples of hollow microspheres which may be used are those which comprise at least one synthetic polymer obtained by polymerization of one or more ethylenically unsaturated monomers to form homopolymers or copolymers of ethylenically unsaturated monomers or copolymers of ethylenically unsaturated monomers and one or more organic groups. Examples of ethylenically unsaturated monomers that may be suitable include, for example, vinylidene chloride, vinyl chloride, acrylonitrile, acrylic acid and its corresponding $C_1$-$C_{20}$ aliphatic or aromatic esters, methacrylic acid and its corresponding $C_1$-$C_{20}$ aliphatic or aromatic esters, acrylamide, methacrylamide, vinyl pyrrolidone, alkenes such as styrene, ethylene, propylene, butylene, methylpentene, 1,3-butadiene, and the like. The polymeric shells of the hollow microspheres may also be formed of suitable synthetic polymers, such as polyesters, polyamides, polyphthalamides, polyimides, polycarbonates, polyketones, cellulose acetate, polysulfones, polyphenylene sulfides, polyphenylene oxides, polylactic acids, polyvinylpyrrolidone, polystyrene, polyacrylonitrile, polyacrylamide, polymethylmethacrylate, polyacrylates, and copolymers of the above-listed polymers. In a particularly preferred embodiment, the deformable polymeric shells of the hollow microspheres are formed of a copolymer of vinylidene chloride, acrylonitrile, and/or methyl methyacrylate.

A preferred example of hollow microspheres are those having deformable polymeric shells comprised of a copolymer of vinylidene chloride, acrylonitrile, and methylmethacrylate with an expandable fluid comprised of isobutane or isopentane may be used, and are commercially available under the trade name of EXPANCEL® from Expancel, Inc. at Duluth, Ga. The EXPANCEL® hollow microspheres are available in various forms, e.g., dry, wet, unexpanded or pre-expanded. Both the dry, unexpanded microspheres (EXPANCEL® DU) and the dry, expanded microspheres (EXPANCEL® DE) can be used in the present invention for entrapping and stabilizing the NIR light-emitting material. The EXPANCEL® DU microspheres have an average particle size ranging from about 6 to about 40 microns and a density of about 1-1.3 g/cm$^3$. The EXPANCEL® DE microspheres have an average particle size ranging from about 20 to about 150 microns and a density of about 0.03-0.07 g/cm$^3$.

Encapsulation may be used to provide controlled or delayed release of the NIR light-emitting material, or it may prevent the release of the NIR light-emitting material entirely without obstructing the NIR light emissions to the skin, scalp or hair. Preferably, the physical and/or chemical properties of the entrapped NIR light-emitting material, pertaining to or associated with their desired activities in the cosmetic or topical compositions are not adversely affected, while the significantly larger microspheres, vesicles, liposomes, and so forth, may impart improved structural and spatial stability.

Microspheres may be coated or otherwise surface-treated with a film-forming material, which forms a liquid-impermeable membrane over each of the microspheres. In this manner, the microspheres are sealed from solvents in the surrounding environment, which may potentially re-swell the polymeric shells of the microspheres and cause the entrapped NIR light-emitting material to be prematurely released. Any material capable of forming a liquid-impermeable membrane, either hydrophilic or hydrophobic, can be used. Suitable materials include film-forming materials such as natural or synthetic homo- or co-polymers comprised of ethylenically unsaturated monomers including acrylic acid, methacrylic acid or their $C_1$-$C_{10}$ alkyl esters, ethylene, propylene, or vinylpyrrolidones; silicone gums, which are organosiloxanes generally having a viscosity ranging from about 200,000 to 10,000,000 centipoise at room temperature; animal, vegetable, silicone or mineral waxes; organic ester or hydrocarbon oils, or silicone resins such as trimethylsiloxy silicate or polymethylsilsesquioxane; cellulosic polymers; fatty acids (e.g. fatty carboxylic acids having from about 6 to 40 carbon atoms that may be liquid, solid or semi-solids at room temperature), fatty alcohols (e.g. alcohols having from 6 to 50 carbon atoms that may be liquid, solid, or semi-solid at room temperature), and inorganic materials. As an example, the film-forming material may comprise an alkyl silicone polymer, for example, a fatty alkylmethylsiloxane, such as cetyl dimethicone, stearyl dimethicone, or behenyl dimethicone, or other modified siloxanes, such as polyoxyalkylenated silicones typically referred to as dimethicone copolyol or cetyl dimethicone copolyol. For example, a polymethylhydrogensiloxane, which is commercially available from Dow Corning Corporation at Midland, Mich. under the trade name of Dow Corning® MH 1107 fluid, may be used as the film-forming material. This polymethylhydrogensiloxane material is a colorless silicone liquid that can be heat cured in the presence of a catalyst (e.g., zinc octoate, iron octoate, dibutyl tin dilaurate, and tin octoate) to form a solid, liquid-impermeable membrane comprised of cross-linked dimethicone over the microspheres. As another example, silicone copolymers commercialized by Dow Corning under the trade name of BIO-PSA, which are formed by reacting a siloxane resin with a diorganosiloxane, may also be used as film-forming materials. Various types of BIO-PSA materials available from Dow Corning may be used, including Dow Corning® 7-4404, 7-4405, and 7-4411 fluids (containing trimethylated silica treated with dimethylsiloxane and dispersed in a cosmetically acceptable solvent, such as octamethyltrisiloxane, isododecane, or decamethyltetrasiloxane).

The compositions of the present invention may contain additional cosmetically and/or dermatologically acceptable ingredients, including such as described hereinbelow.

Suitable serums or gels will generally comprise from about 1-99% water, and optionally from about 0.001-30% of an aqueous phase thickening agent. The other ingredients mentioned herein may be present in the percentage ranges set forth.

Typical skin creams or lotions comprise from about 5-98% water, 1-85% oil, and from about 0.1 to 20% of one or more surfactants. Preferably the surfactants are nonionic and may be in the form of silicones or organic nonionic surfactants.

Typical color cosmetic compositions such as foundations, blush, eyeshadow, and the like, will preferably contain from about 5-98% water, 1-85% oil, and from about 0.1 to 20% of one or more surfactants in addition to from about 0.1 to 65% of particulates which are pigments or a combination of pigments and powders.

In the case where the compositions are in the form of aqueous solutions, dispersions or emulsions, in addition to water, the aqueous phase may contain one or more aqueous phase structuring agents, that is, an agent that increases the viscosity, or thickens, the aqueous phase of the composition. This is particularly desirable when the composition is in the form of a serum or gel. The aqueous phase structuring agent should be compatible with the NIR-emitting material and also compatible with the other ingredients in the formulation. Suitable ranges of aqueous phase structuring agent, if present, are from about 0.01 to 30%, preferably from about 0.1 to 20%, more preferably from about 0.5 to 15% by weight of the total composition. Examples of such agents include various acrylate-based thickening agents, natural or synthetic gums, polysaccharides, and the like, including but not limited to those set forth below. The aqueous phase thickening agent also contributes to stabilizing ingredients in the composition and improving penetration into the stratum corneum. Such structuring agents may include the following:

A. Polysaccharides

Polysaccharides may be suitable aqueous phase thickening agents. Examples of such polysaccharides include naturally derived materials such as agar, agarose, alicaligenes polysaccharides, algin, alginic acid, acacia gum, amylopectin, chitin, dextran, *cassia* gum, cellulose gum, gelatin, gellan gum, hyaluronic acid, hydroxyethyl cellulose, methyl cellulose, ethyl cellulose, pectin, sclerotium gum, xanthan gum, pectin, trehelose, gelatin, and so on.

B. Acrylate Polymers

Also suitable are different types of synthetic polymeric thickeners. One type includes acrylic polymeric thickeners comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alky methacrylate, and mixtures thereof are suitable. In one embodiment the A monomer comprises one or more of acrylic acid or methacrylic acid, and the B monomer is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. The acrylic copolymer may be supplied in an aqueous solution having a solids content ranging from about 10-60%, preferably 20-50%, more preferably 25-45% by weight of the polymer, with the remainder water. The composition of the acrylic copolymer may contain from about 0.1-99 parts of the A monomer, and about 0.1-99 parts of the B monomer. Acrylic polymer solutions include those sold by Seppic, Inc., under the trade name Capigel. Also suitable are acrylic polymeric thickeners that are copolymers of A, B, and C monomers wherein A and B are as defined above, and C has the general formula:

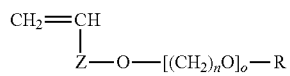

wherein Z is $—(CH_2)_m$; wherein m is 1-10, n is 2-3, o is 2-200, and R is a $C_{10-30}$ straight or branched chain alkyl. Examples of the secondary thickening agent above, are copolymers where A and B are defined as above, and C is CO, and wherein n, o, and R are as above defined. Examples of such secondary thickening agents include acrylates/steareth-20 methacrylate copolymer, which is sold by Rohm & Haas under the trade name Acrysol ICS-1.

Also suitable are acrylate-based anionic amphiphilic polymers containing at least one hydrophilic unit and at least one allyl ether unit containing a fatty chain. Preferred are those where the hydrophilic unit contains an ethylenically unsaturated anionic monomer, more specifically a vinyl carboxylic acid such as acrylic acid, methacrylic acid or mixtures thereof, and where the allyl ether unit containing a fatty chain corresponds to the monomer of the formula:

in which R' denotes H or $CH_3$, B denotes the ethylenoxy radical, n is zero or an integer ranging from 1 to 100, R denotes a hydrocarbon radical selected from alkyl, arylalkyl, aryl, alkylaryl and cycloalkyl radicals which contain from 8 to 30 carbon atoms, preferably from 10 to 24, and even more particularly from 12 to 18 carbon atoms. More preferred in this case is where R' denotes H, n is equal to 10 and R denotes a stearyl ($C_{18}$) radical. Anionic amphiphilic polymers of this type are described and prepared in U.S. Pat. Nos. 4,677,152 and 4,702,844, both of which are hereby incorporated by reference in their entirety. Among these anionic amphiphilic polymers, polymers formed of 20 to 60% by weight acrylic acid and/or methacrylic acid, of 5 to 60% by weight lower alkyl methacrylates, of 2 to 50% by weight allyl ether containing a fatty chain as mentioned above, and of 0 to 1% by weight of a crosslinking agent which is a well-known copolymerizable polyethylenic unsaturated monomer, for instance diallyl phthalate, allyl (meth)acrylate, divinylbenzene, (poly) ethylene glycol dimethacrylate and methylene-bisacrylamide. Commercial examples of such polymers are crosslinked terpolymers of methacrylic acid, of ethyl acrylate, of polyethylene glycol (having 10 EO units) ether of stearyl alcohol or steareth-10, in particular those sold by the company Allied Colloids under the names SALCARE SC80 and SALCARE SC90, which are aqueous emulsions containing 30% of a crosslinked terpolymer of methacrylic acid, of ethyl acrylate and of steareth-10 allyl ether (40/50/10).

Also suitable are acrylate copolymers such as Polyacrylate-3 which is a copolymer of methacrylic acid, methylmethacrylate, methylstyrene isopropylisocyanate, and PEG-40 behenate monomers; Polyacrylate-10 which is a copolymer of sodium acryloyldimethyltaurate, sodium acrylate, acrylamide and vinyl pyrrolidone monomers; or Polyacrylate-11, which is a copolymer of sodium acryloyldimethylacryloyldimethyl taurate, sodium acrylate, hydroxyethyl acrylate, lauryl acrylate, butyl acrylate, and acrylamide monomers.

Also suitable are crosslinked acrylate based polymers where one or more of the acrylic groups may have substituted long chain alkyl (such as 6-40, 10-30, and the like) groups, for example acrylates/$C_{10-30}$ alkyl acrylate crosspolymer which is a copolymer of $C_{10-30}$ alkyl acrylate and one or more monomers of acrylic acid, methacrylic acid, or one of their simple esters crosslinked with the allyl ether of sucrose or the allyl ether of pentaerythritol. Such polymers are commonly sold under the Carbopol or Pemulen tradenames and have the CTFA name carbomer.

One particularly suitable type of aqueous phase thickening agent are acrylate-based polymeric thickeners sold by Clariant under the Aristoflex trademark such as Aristoflex AVC, which is ammonium acryloyldimethyltaurate/VP copolymer; Aristoflex AVL which is the same polymer as found in AVC dispersed in a mixture containing caprylic/capric triglyceride, trilaureth-4, and polyglyceryl-2 sesquiisostearate; or Aristoflex HMB which is ammonium acryloyldimethyltaurate/beheneth-25 methacrylate crosspolymer, and the like.

C. High Molecular Weight PEG or Polyglycerins

Also suitable as the aqueous phase thickening agents are various polyethylene glycols (PEG) derivatives where the degree of polymerization ranges from 1,000 to 200,000. Such ingredients are indicated by the designation "PEG" followed by the degree of polymerization in thousands, such as PEG-45M, which means PEG having 45,000 repeating ethylene oxide units. Examples of suitable PEG derivatives include PEG 2M, 5M, 7M, 9M, 14M, 20M, 23M, 25M, 45M, 65M, 90M, 115M, 160M, 180M, and the like.

Also suitable are polyglycerins which are repeating glycerin moieties where the number of repeating moieties ranges from 15 to 200, preferably from about 20-100. Examples of suitable polyglycerins include those having the CTFA names polyglycerin-20, polyglycerin-40, and the like.

In the event the compositions of the invention are in anhydrous or emulsion form, the composition will comprise an oil phase. Oily ingredients are desirable for the skin moisturizing and protective properties. Suitable oils include silicones, esters, vegetable oils, synthetic oils, including but not limited to those set forth herein. The oils may be volatile or nonvolatile, and are preferably in the form of a pourable liquid at room temperature. The term "volatile" means that the oil has a measurable vapor pressure or a vapor pressure of at least about 2 mm. of mercury at 20° C. The term "nonvolatile" means that the oil has a vapor pressure of less than about 2 mm. of mercury at 20° C. Suitable oils may include the following:

A. Volatile Oils

Suitable volatile oils generally have a viscosity ranging from about 0.5 to 5 centistokes 25° C. and include linear silicones, cyclic silicones, paraffinic hydrocarbons, or mixtures thereof. Volatile oils may be used to promote more rapid drying of the skin care composition after it is applied to skin. Volatile oils are more desirable when the skin care products are being formulated for consumers that have combination or oily skin. The term "combination" with respect to skin type means skin that is oily in some places on the face (such as the T-zone) and normal in others.

1. Volatile Silicones

Cyclic silicones are one type of volatile silicone that may be used in the composition. Such silicones have the general formula:

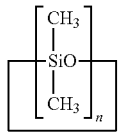

where n=3-6, preferably 4, 5, or 6.
Also suitable are linear volatile silicones, for example, those having the general formula:

where n=0, 1, 2, 3, 4, or 5, preferably 0, 1, 2, 3, or 4.

Cyclic and linear volatile silicones are available from various commercial sources including Dow Corning Corporation and General Electric. The Dow Corning linear volatile silicones are sold under the tradenames Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C. Suitable branched volatile silicones include alkyl trimethicones such as methyl trimethicone, a branched volatile silicone having the general formula:

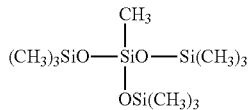

Methyl trimethicone may be purchased from Shin-Etsu Silicones under the tradename TMF-1.5, having a viscosity of 1.5 centistokes at 25° C.

2. Volatile Paraffinic Hydrocarbons

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference.

Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISO-PARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

B. Non-Volatile Oils

A variety of nonvolatile oils are also suitable for use in the compositions of the invention. The nonvolatile oils generally have a viscosity of greater than about 5 to 10 centistokes at 25° C., and may range in viscosity up to about 1,000,000 centipoise at 25° C. Examples of nonvolatile oils include, but are not limited to:

1. Esters

Suitable esters are mono-, di-, and triesters. The composition may comprise one or more esters selected from the group, or mixtures thereof.

(a) Monoesters

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, stearyl lactate, stearyl octanoate, stearyl stearate, isononyl isononanoate, and so on.

(b). Diesters

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

(c). Triesters

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety.

2. Hydrocarbon Oils

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

3. Glyceryl Esters of Fatty Acids

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, *camelina sativa oil*, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

4. Nonvolatile Silicones

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone.

For example, such nonvolatile silicones may have the following general formula:

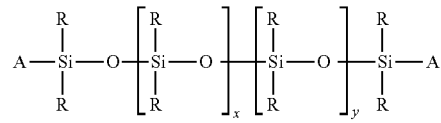

wherein R and R' are each independently $C_{1-30}$ straight or branched chain, saturated or unsaturated alkyl, phenyl or aryl, trialkylsiloxy, and x and y are each independently 1-1,000,000; with the proviso that there is at least one of either x or y, and A is alkyl siloxy endcap unit. Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the trade names Abil Wax 9801, or 9814.

5. Fluorinated Oils

Various types of fluorinated oils may also be suitable for use in the compositions including but not limited to fluorinated silicones, fluorinated esters, or perfluoropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. Perfluoropolyethers include those disclosed in U.S. Pat. Nos. 5,183,589, 4,803,067, 5,183,588, all of which are hereby incorporated by reference, which are commercially available from Montefluos under the trademark Fomblin.

In the case where the composition is anhydrous or in the form of an emulsion, it may be desirable to include one or more oil phase structuring agents in the cosmetic composition. The term "oil phase structuring agent" means an ingredient or combination of ingredients, soluble or dispersible in the oil phase, which will increase the viscosity, or structure, the oil phase. The oil phase structuring agent is compatible with the NIR-emitting, particularly if dispersed in the nonpolar oils forming the oil phase of the composition. The term "compatible" means that the oil phase structuring agent and NIR-emitting material are capable of being formulated into a cosmetic product that is generally stable. The structuring agent may be present in an amount sufficient to provide a liquid composition with increased viscosity, a semi-solid, or in some cases a solid composition that may be self-supporting. The structuring agent itself may be present in the liquid, semi-solid, or solid form. Suggested ranges of structuring agent are from about 0.01 to 70%, preferably from about 0.05 to 50%, more preferably from about 0.1-35% by weight of the total composition. Suitable oil phase structuring agents include those that are silicone based or organic based. They may be polymers or non-polymers, synthetic, natural, or a combination of both. Such oil structuring agents may include the following:

A. Silicone Structuring Agents

A variety of oil phase structuring agents may be silicone based, such as silicone elastomers, silicone gums, silicone waxes, and linear silicones having a degree of polymerization that provides the silicone with a degree of viscosity such that when incorporated into the cosmetic composition it is capable of increasing the viscosity of the oil phase. Examples of silicone structuring agents include, but are not limited to:

1. Silicone Elastomers

Silicone elastomers suitable for use in the compositions of the invention include those that are formed by addition reaction-curing, by reacting an SiH-containing diorganosiloxane and an organopolysiloxane having terminal olefinic unsaturation, or an alpha-omega diene hydrocarbon, in the presence of a platinum metal catalyst. Such elastomers may also be formed by other reaction methods such as condensation-curing organopolysiloxane compositions in the presence of an organotin compound via a dehydrogenation reaction between hydroxyl-terminated diorganopolysiloxane and SiH-containing diorganopolysiloxane or alpha omega diene; or by condensation-curing organopolysiloxane compositions in the presence of an organotin compound or a titanate ester using a condensation reaction between an hydroxyl-terminated diorganopolysiloxane and a hydrolysable organosiloxane; peroxide-curing organopolysiloxane compositions which thermally cure in the presence of an organoperoxide catalyst.

One type of elastomer that may be suitable is prepared by addition reaction-curing an organopolysiloxane having at least 2 lower alkenyl groups in each molecule or an alpha-omega diene; and an organopolysiloxane having at least 2 silicon-bonded hydrogen atoms in each molecule; and a platinum-type catalyst. While the lower alkenyl groups such as vinyl, can be present at any position in the molecule, terminal olefinic unsaturation on one or both molecular terminals is preferred. The molecular structure of this component may be straight chain, branched straight chain, cyclic, or network. These organopolysiloxanes are exemplified by methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl)polysiloxanes, and dimethylvinylsiloxy-terminated dimethylsiloxane-methyl(3,3,-trifluoropropyl)siloxane copolymers, decadiene, octadiene, heptadiene, hexadiene, pentadiene, or tetradiene, or tridiene.

Curing proceeds by the addition reaction of the silicon-bonded hydrogen atoms in the dimethyl methylhydrogen siloxane, with the siloxane or alpha-omega diene under catalysis using the catalyst mentioned herein. To form a highly crosslinked structure, the methyl hydrogen siloxane must contain at least 2 silicon-bonded hydrogen atoms in each molecule in order to optimize function as a crosslinker.

The catalyst used in the addition reaction of silicon-bonded hydrogen atoms and alkenyl groups, and is concretely exemplified by chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum.

Examples of suitable silicone elastomers for use in the compositions of the invention may be in the powder form, or dispersed or solubilized in solvents such as volatile or nonvolatile silicones, or silicone compatible vehicles such as paraffinic hydrocarbons or esters. Examples of silicone elastomer powders include vinyl dimethicone/methicone silesquioxane crosspolymers like Shin-Etsu's KSP-100, KSP-101, KSP-102, KSP-103, KSP-104, KSP-105, hybrid silicone powders that contain a fluoroalkyl group like Shin-Etsu's KSP-200 which is a fluoro-silicone elastomer, and hybrid silicone powders that contain a phenyl group such as Shin-Etsu's KSP-300, which is a phenyl substituted silicone elastomer; and Dow Corning's DC 9506. Examples of silicone elastomer powders dispersed in a silicone compatible vehicle include dimethicone/vinyl dimethicone crosspolymers supplied by a variety of suppliers including Dow Corning Corporation under the tradenames 9040 or 9041, GE Silicones under the tradename SFE 839, or Shin-Etsu Silicones under the tradenames KSG-15, 16, 18. KSG-15 has the CTFA name cyclopentasiloxane/dimethicone/vinyl dimethicone crosspolymer. KSG-18 has the INCI name phenyl trimethicone/dimethicone/phenyl vinyl dimethicone crossopolymer. Silicone elastomers may also be purchased from Grant Industries under the Gransil trademark. Also suitable are silicone elastomers having long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44. Cross-linked organopolysiloxane elastomers useful in the present invention and processes for making them are further described in U.S. Pat. No. 4,970,252; U.S. Pat. No. 5,760,116; U.S. Pat. No. 5,654,362; and Japanese Patent Application JP 61-18708; each of which is herein incorporated by reference in its entirety. It is particularly desirable to incorporate silicone elastomers into the compositions of the invention because they provide excellent "feel" to the composition, are very stable in cosmetic formulations, and relatively inexpensive.

2. Silicone Gums

Also suitable for use as an oil phase structuring agent are one or more silicone gums. The term "gum" means a silicone polymer having a degree of polymerization sufficient to provide a silicone having a gum-like texture. In certain cases the silicone polymer forming the gum may be crosslinked. The silicone gum typically has a viscosity ranging from about 500,000 to 100 million cst at 25° C., preferably from about 600,000 to 20 million, more preferably from about 600,000 to 12 million cst. All ranges mentioned herein include all subranges, e.g. 550,000; 925,000; 3.5 million.

The silicone gums that are used in the compositions include, but are not limited to, those of the general formula:

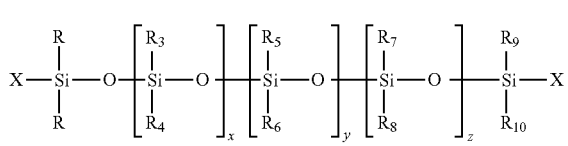

wherein $R_1$ to $R_9$ are each independently an alkyl having 1 to 30 carbon atoms, aryl, or aralkyl; and X is OH or a $C_{1-30}$ alkyl, or vinyl; and wherein x, y, or z may be zero with the proviso that no more than two of x, y, or z are zero at any one time, and further that x, y, and z are such that the silicone gum has a viscosity of at least about 500,000 cst, ranging up to about 100 million centistokes at 25° C. Preferred is where R is methyl or OH.

Such silicone gums may be purchased in pure form from a variety of silicone manufacturers including Wacker-Chemie or Dow Corning, and the like. Such silicone gums include those sold by Wacker-Belsil under the trade names CM3092, Wacker-Belsil 1000, or Wacker-Belsil DM 3096. A silicone gum where X is OH, also referred to as dimethiconol, is available from Dow Corning Corporation under the trade name 1401. The silicone gum may also be purchased in the form of a solution or dispersion in a silicone compatible vehicle such as volatile or nonvolatile silicone. An example of such a mixture may be purchased from Barnet Silicones under the HL-88 tradename, having the INCI name dimethicone.

3. Silicone Waxes

Another type of oily phase structuring agent includes silicone waxes that are typically referred to as alkyl silicone waxes which are semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from DeGussa Care & Surface Specialties under the tradename Abil Wax 9800 or from Dow Corning under the tradename 2503. Another example is bis-stearyl dimethicone, which may be purchased from Gransil Industries under the tradename Gransil A-18, or behenyl dimethicone, behenoxy dimethicone.

4. Polyamides or Silicone Polyamides

Also suitable as oil phase structuring agents are various types of polymeric compounds such as polyamides or silicone polyamides.

The term silicone polyamide means a polymer comprised of silicone monomers and monomers containing amide groups as further described herein. The silicone polyamide preferably comprises moieties of the general formula:

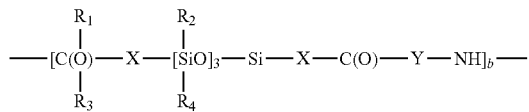

X is a linear or branched alkylene having from about 1-30 carbon atoms; $R_1$, $R_2$, $R_3$, and $R_4$ are each independently $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

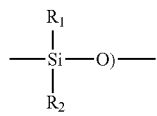

and Y is:
(a) a linear or branched alkylene having from about 1-40 carbon atoms which may be substituted with:
  (i) one or more amide groups having the general formula $R_1CONR_1$, or
  (ii) $C_{5-6}$ cyclic ring, or
  (iii) phenylene which may be substituted with one or more $C_{1-10}$ alkyl groups, or
  (iv) hydroxy, or
  (v) $C_{3-8}$ cycloalkane, or
  (vi) $C_{1-20}$ alkyl which may be substituted with one or more hydroxy groups, or
  (vii) $C_{1-10}$ alkyl amines; or
(b) $TR_5R_6R_7$
wherein $R_5$, $R_6$, and $R_7$, are each independently a $C_{1-10}$ linear or branched alkylenes, and T is $CR_8$ wherein $R_8$ is hydrogen, a trivalent atom N, P, or Al, or a $C_{1-30}$ straight or branched chain alkyl which may be substituted with one or more hydroxyl or halogen groups; phenyl which may be substituted with one or more $C_{1-30}$ alkyl groups, halogen, hydroxyl, or alkoxy groups; or a siloxane chain having the general formula:

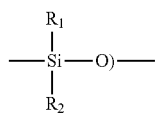

Preferred is where $R_1$, $R_2$, $R_3$, and $R_4$ are $C_{1-10}$, preferably methyl; and X and Y are a linear or branched alkylene. Preferred are silicone polyamides having the general formula:

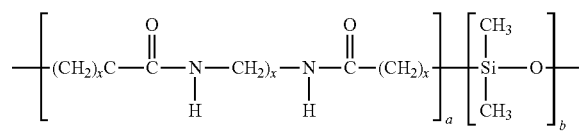

wherein a and b are each independently sufficient to provide a silicone polyamide polymer having a melting point ranging from about 60 to 120° C., and a molecular weight ranging from about 40,000 to 500,000 Daltons. One type of silicone polyamide that may be used in the compositions of the invention may be purchased from Dow Corning Corporation under the tradename Dow Corning 2-8178 gellant which has the CTFA name nylon-611/dimethicone copolymer which is sold in a composition containing PPG-3 myristyl ether.

Also suitable are polyamides such as those purchased from Arizona Chemical under the tradenames Uniclear and Sylvaclear. Such polyamides may be ester terminated or amide terminated. Examples of ester terminated polyamides include, but are not limited to those having the general formula:

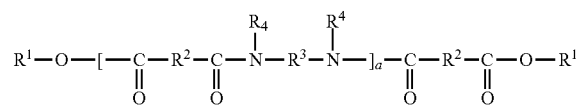

wherein n denotes a number of amide units such that the number of ester groups ranges from about 10% to 50% of the total number of ester and amide groups; each $R_1$ is independently an alkyl or alkenyl group containing at least 4 carbon atoms; each $R_2$ is independently a $C_{4-42}$ hydrocarbon group, with the proviso that at least 50% of the $R_2$ groups are a $C_{30}$-42 hydrocarbon; each $R_3$ is independently an organic group containing at least 2 carbon atoms, hydrogen atoms and optionally one or more oxygen or nitrogen atoms; and each $R_4$ is independently a hydrogen atom, a $C_{1-10}$ alkyl group or a direct bond to $R_3$ or to another $R_4$, such that the nitrogen atom to which $R_3$ and $R_4$ are both attached forms part of a heterocyclic structure defined by $R_4$—N—$R_3$, with at least 50% of the groups $R_4$ representing a hydrogen atom.

General examples of ester and amide terminated polyamides that may be used as oil phase gelling agents include those sold by Arizona Chemical under the tradenames Sylvaclear A200V or A2614V, both having the CTFA name ethylenediamine/hydrogenated dimer dilinoleate copolymer/bis-di-$C_{14-18}$ alkyl amide; Sylvaclear AF1900V; Sylvaclear C75V having the CTFA name bis-stearyl ethylenediamine/neopentyl glycol/stearyl hydrogenated dimer dilinoleate copolymer; Sylvaclear PA1200V having the CTFA name Polyamide-3; Sylvaclear PE400V; Sylvaclear WF1500V; or Uniclear, such as Uniclear 100VG having the INCI name ethylenediamine/stearyl dimer dilinoleate copolymer; or ethylenediamine/stearyl dimer ditallate copolymer. Other examples of suitable polyamides include those sold by Henkel under the Versamid trademark (such as Versamid 930, 744, 1655), or by Olin Mathieson Chemical Corp. under the brand name Onamid S or Onamid C.

5. Natural or Synthetic Organic Waxes

Also suitable as the oil phase structuring agent may be one or more natural or synthetic waxes such as animal, vegetable, or mineral waxes. Preferably such waxes will have a higher melting point such as from about 50 to 150° C., more preferably from about 65 to 100° C. Examples of such waxes include waxes made by Fischer-Tropsch synthesis, such as polyethylene or synthetic wax; or various vegetable waxes such as bayberry, candelilla, ozokerite, acacia, beeswax, ceresin, cetyl esters, flower wax, citrus wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, grape wax, and polyalkylene glycol derivatives thereof such as PEG6-20 beeswax, or PEG-12 carnauba wax; or fatty acids or fatty alcohols, including esters thereof, such as hydroxystearic acids (for example 12-hydroxy stearic acid), tristearin, tribehenin, and so on.

6. Montmorillonite Minerals

One type of structuring agent that may be used in the composition comprises natural or synthetic montmorillonite minerals such as hectorite, bentonite, and quaternized derivatives thereof, which are obtained by reacting the minerals with a quaternary ammonium compound, such as stearalkonium bentonite, hectorites, quaternized hectorites such as Quaternium-18 hectorite, attapulgite, carbonates such as propylene carbonate, bentones, and the like.

7. Silicas and Silicates

Another type of structuring agent that may be used in the compositions are silicas, silicates, silica silylate, and alkali metal or alkaline earth metal derivatives thereof. These silicas and silicates are generally found in the particulate form and include silica, silica silylate, magnesium aluminum silicate, and the like.

The composition may contain one or more surfactants, especially if in the emulsion form. However, such surfactants may be used if the compositions are anhydrous also, and will assist in dispersing ingredients that have polarity, for example pigments. Such surfactants may be silicone or organic based. The surfactants will aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

A. Silicone Surfactants

Suitable silicone surfactants include polyorganosiloxane polymers that have amphiphilic properties, for example contain hydrophilic radicals and lipophilic radicals. These silicone surfactants may be liquids or solids at room temperature.

1. Dimethicone Copolyols or Alkyl Dimethicone Copolyols

One type of silicone surfactant that may be used is generally referred to as dimethicone copolyol or alkyl dimethicone copolyol. This surfactant is either a water-in-oil or oil-in-water surfactant having an Hydrophile/Lipophile Balance (HLB) ranging from about 2 to 18. Preferably the silicone surfactant is a nonionic surfactant having an HLB ranging from about 2 to 12, preferably about 2 to 10, most preferably about 4 to 6. The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, and mixtures thereof. The term "lipophilic radical" means an organic radical that, when substituted onto the organosiloxane polymer backbone, confers lipophilic properties to the substituted portion of the polymer. Examples of organic radicals that will confer lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof.

One type of suitable silicone surfactant has the general formula:

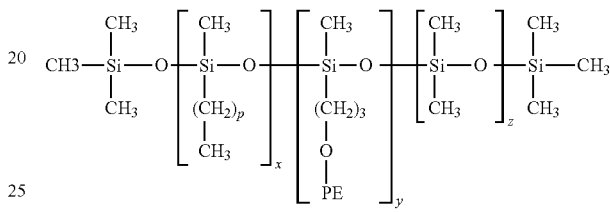

wherein p is 0-40 (the range including all numbers between and subranges such as 2, 3, 4, 13, 14, 15, 16, 17, 18, etc.), and PE is $(-C_2H_4O)_a-(-C_3H_6O)_b-H$ wherein a is 0 to 25, b is 0-25 with the proviso that both a and b cannot be 0 simultaneously, x and y are each independently ranging from 0 to 1 million with the proviso that they both cannot be 0 simultaneously. In one preferred embodiment, x, y, z, a, and b are such that the molecular weight of the polymer ranges from about 5,000 to about 500,000, more preferably from about 10,000 to 100,000, and is most preferably approximately about 50,000 and the polymer is generically referred to as dimethicone copolyol.

One type of silicone surfactant is wherein p is such that the long chain alkyl is cetyl or lauryl, and the surfactant is called, generically, cetyl dimethicone copolyol or lauryl dimethicone copolyol respectively.

In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Corning under the trade name Dow Corning 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dow Corning 190 Surfactant having the CTFA name PEG/PPG-18/18 dimethicone; or Dow Corning 193 Fluid, Dow Corning 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

2. Crosslinked Silicone Surfactants Also suitable are various types of crosslinked silicone surfactants that are often referred to as emulsifying elastomers. They are typically prepared as set forth above with respect to the section "silicone elastomers" except that the silicone elastomers will contain at least one hydrophilic moiety such as polyoxyalkylenated groups. Typically these polyoxyalkylenated silicone elastomers are crosslinked organopolysiloxanes that may be obtained by a crosslinking addition reaction of diorganopolysiloxane comprising at least one hydrogen bonded to silicon and of a polyoxyalkylene comprising at least two ethylenically unsaturated groups. In at least one embodiment, the polyoxyalkylenated crosslinked organo-polysiloxanes are obtained by a crosslinking addition reaction of a diorganopolysiloxane comprising at least two hydrogens each bonded to a silicon, and a polyoxyalkylene comprising at least two ethylenically unsaturated groups, optionally in the presence of a platinum catalyst, as described, for example, in U.S. Pat. No. 5,236,986, U.S. Pat. No. 5,412,004, U.S. Pat. No. 5,837, 793 and U.S. Pat. No. 5,811,487, the contents of which are hereby incorporated by reference in their entireties.

Polyoxyalkylenated silicone elastomers that may be used in at least one embodiment of the invention include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Corning under the tradenames 9010 and DC9011.

One preferred crosslinked silicone elastomer emulsifier is dimethicone/PEG-10/15 crosspolymer, which provides excellent aesthetics due to its elastomeric backbone, but also surfactancy properties.

B. Organic Nonionic Surfactants

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanoates such as PEG dipolyhydroxystearate wherein the number of repeating ethylene glycol units ranges from 3 to 1000.

Also suitable as nonionic surfactants are those formed by the reaction of a carboxylic acid with an alkylene oxide or with a polymeric ether. The resulting products have the general formula:

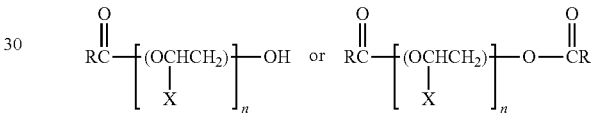

where RCO is the carboxylic ester radical, X is hydrogen or lower alkyl, and n is the number of polymerized alkoxy groups. In the case of the diesters, the two RCO-groups do not need to be identical. Preferably, R is a $C_{6-30}$ straight or branched chain, saturated or unsaturated alkyl, and n is from 1-100.

Monomeric, homopolymeric, or block copolymeric ethers are also suitable as nonionic surfactants. Typically, such ethers are formed by the polymerization of monomeric alkylene oxides, generally ethylene or propylene oxide. Such polymeric ethers have the following general formula:

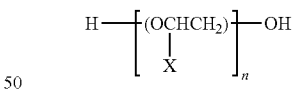

wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with $C_{6-30}$, preferably C12-22 fatty acids. Examples of such ingredients include Polysorbates 20-85, sorbitan oleate, sorbitan sesquioleate, sorbitan palmitate, sorbitan sesquiisostearate, sorbitan stearate, and so on.

Certain types of amphoteric, zwitterionic, or cationic surfactants may also be used in the compositions. Descriptions of such surfactants are set forth in U.S. Pat. No. 5,843,193, which is hereby incorporated by reference in its entirety.

It may be desirable to include one or more penetration enhancers in the composition. Penetration enhancers are ingredients that enhance the penetration of the NIR light-emitting material and/or other skin, scalp or hair benefit agent, if present, into the keratinous surface to which the composition is applied. If present, suitable penetration enhancers may range from about 0.001 to 30%, preferably from about 0.005 to 25%, more preferably from about 0.01 to 20%. Suitable penetration enhancers include, but are not limited to, lipophilic materials such as saturated or unsaturated $C_{6\text{-}40}$ straight or branched chain fatty acids, or saturated or unsaturated $C_{6\text{-}40}$ straight or branched chain fatty alcohols. Examples include oleic acid, linoleic acid, stearic acid, oleyl alcohol, linoleyl alcohol, and the like.

It may be desirable to include one or more film forming ingredients in the cosmetic compositions of the invention. Suitable film formers are ingredients that contribute to formation of a film on the keratinous surface. In some cases the film formers may provide films that provide long wearing or transfer resistant properties such that the cosmetic applied to the keratinous surface will remain for periods of time ranging from 3 to 16 hours. If present, such film formers may range from about 0.01 to 50%, preferably from about 0.1 to 40%, more preferably from about 0.5 to 35% by weight of the total composition. The film formers are most often found in the polymeric form and may be natural or synthetic polymers. If synthetic, silicone polymers, organic polymers or copolymers of silicones and organic groups may be acceptable. Suitable film formers include, but are not limited to:

A. Silicone Resins

One particularly suitable type of silicone film former is a silicone resin. Silicone resins are generally highly crosslinked structures comprising combinations of M, D, T, and Q units. The term "M" means a monofunctional siloxy unit having the general formula:

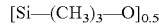
[Si—(CH$_3$)$_3$—O]$_{0.5}$

In cases where the M unit is other than methyl (such as ethyl, propyl, ethoxy, etc.) the M unit may have a prime after it, e.g. M'.

The term "D" means a difunctional siloxy unit having the general formula:

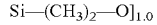
Si—(CH$_3$)$_2$—O]$_{1.0}$

The difunctional unit may be substituted with alkyl groups other than methyl, such as ethyl, propyl, alkylene glycol, and the like, in which case the D unit may be referred to as D', with the prime indicating a substitution.

The term "T" means a trifunctional siloxy unit having the general formula:

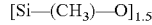
[Si—(CH$_3$)—O]$_{1.5}$

The trifunctional unit may be substituted with substituents other than methyl, in which case it may be referred to as T'.

The term "Q" refers to a quadrifunctional siloxy unit having the general formula:

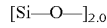
[Si—O—]$_{2.0}$

The silicone resins that may be used as film formers in the compositions of the invention preferably comprise highly crosslinked combinations of M, T, and Q units. Examples of such resins include trimethylsiloxysilicate which can be purchased from Dow Corning Corporation as 749 Fluid, or from GE Silicones under the SR-1000 trade name. Also suitable is a silicone resin that contains a large percentage of T groups, such as MK resin sold by Wacker-Chemie, having the CTFA name polymethylsilsesquioxane.

B. Copolymers of Silicone and Organic Monomers

Also suitable for use as the film formers are copolymers of silicone and organic monomers such as acrylates, methacrylates, and the like. Examples of such suitable film forming polymers include those commonly referred to as silicone acrylate or vinyl silicone copolymers, such as those sold by 3M under the brand name "Silicone Plus" polymers such as SA-70, having the CTFA name Polysilicone-7 and is a copolymer of isobutylmethacrylate and n-butyl endblocked polydimethylsiloxane propyl methacrylate; or VS-70 having the CTFA name Polysilicone-6, which is a copolymer of dimethylsiloxane and methyl-3 mercaptopropyl siloxane reacted with isobutyl methacrylate; or VS-80, having the CTFA name Polysilicone-8, which has the general structure:

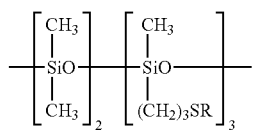

where R represents the acrylates copolymer radical.

C. Organic Polymers

Also suitable as film formers include various types of organic polymers such as polymers formed from acrylic acid, methacrylic acid, or their simple $C_{1\text{-}10}$ carboxylic acid esters, such as methyl methacrylate, methyl acrylate, and the like.

Also suitable are various types of natural polymers such as shellac, natural resins, chitin, and the like.

The compositions of the invention may contain particulate materials in the form of pigments, inert particulates, or mixtures thereof. If present, suggested ranges are from about 0.01-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition. Suitable particulate materials may include the following:

A. Powders

The particulate matter may be colored or non-colored (for example white) non-pigmented powders. Suitable non-pigmented powders include, but are not limited to, bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

B. Pigments

The particulate materials may comprise various organic and/or inorganic pigments. The organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

The composition may contain 0.001-8%, preferably 0.01-6%, more preferably 0.05-5% by weight of the total composition of preservatives. A variety of preservatives are suitable, including, but not limited to, benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, calcium benzoate, calcium propionate, caprylyl glycol, biguanide derivatives, phenoxyethanol, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and the like. In one preferred embodiment the composition is free of parabens.

It may also be desirable to include one or more humectants in the composition. If present, such humectants may range from about 0.001 to 25%, preferably from about 0.005 to 20%, more preferably from about 0.1 to 15% by weight of the total composition. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectants used in the composition of the invention are $C_{1-6}$, preferably $C_{2-4}$ alkylene glycols, most particularly butylene glycol.

It may be desirable to include one or more botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, *Padina pavonica* extract, *Thermus thermophilis* ferment extract, *Camelina sativa* seed oil, *Boswellia serrata* extract, olive extract, *Aribodopsis thaliana* extract, *Acacia dealbata* extract, *Acer saccharinum* (sugar maple), acidopholus, acorus, *aesculus, agaricus*, agave, agrimonia, algae, aloe, citrus, *brassica*, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza glabra, Salix nigra, Macrocycstis pyrifera, Pyrus malus, Saxifraga sarmentosa, Vitis vinifera, Morus nigra, Scutellaria baicalensis, Anthemis nobilis, Salvia sclarea, Rosmarinus officinalis, Citrus medica Limonum, Panax, Ginseng, Siegesbeckia orientalis, Fructus mume, Ascophyllum nodosum*, Bifida Ferment lysate, *Glycine soja* extract, *Beta vulgaris, Haberlea rhodopensis, Polygonum cuspidatum, Citrus Aurantium dulcis, Vitis vinifera, Selaginella tamariscina, Humulus lupulus, Citrus reticulata* Peel, *Punica granatum, Asparagopsis, Curcuma longa, Menyanthes trifoliata, Helianthus annuus, Hordeum vulgare, Cucumis sativus, Evernia prunastri, Evernia furfuracea*, and mixtures thereof.

It may also be desirable to include one or more sunscreens in the compositions of the invention. Such sunscreens include chemical UVA or UVB sunscreens or physical sunscreens in the particulate form. Inclusion of sunscreens in the compositions will provide additional protection to skin during daylight hours and promote the effectiveness of the NIR-emitting material and/or skin or hair benefit agents on the skin or in the hair follicle. Such sunscreen compounds may include the following:

A. UVA Chemical Sunscreens

If desired, the composition may comprise one or more UVA sunscreens. The term "UVA sunscreen" means a chemical compound that blocks UV radiation in the wavelength range of about 320 to 400 nm. Preferred UVA sunscreens are dibenzoylmethane compounds having the general formula:

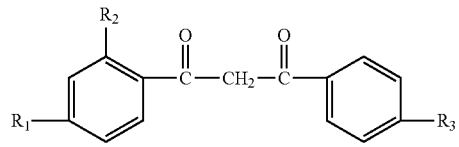

wherein $R_1$ is H, OR and NRR wherein each R is independently H, $C_{1-20}$ straight or branched chain alkyl; $R_2$ is H or OH; and $R_3$ is H, $C_{1-20}$ straight or branched chain alkyl.

Preferred is where $R_1$ is OR where R is a $C_{1-20}$ straight or branched alkyl, preferably methyl; $R_2$ is H; and $R_3$ is a $C_{1-20}$ straight or branched chain alkyl, more preferably, butyl.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercial available from Givaudan-Roure under the trademark Parsol 1789, and Merck & Co. under the tradename Eusolex 9020.

Other types of UVA sunscreens include dicamphor sulfonic acid derivatives, such as ecamsule, a sunscreen sold under the trade name Mexoryl™, which is terephthalylidene dicamphor sulfonic acid, having the formula:

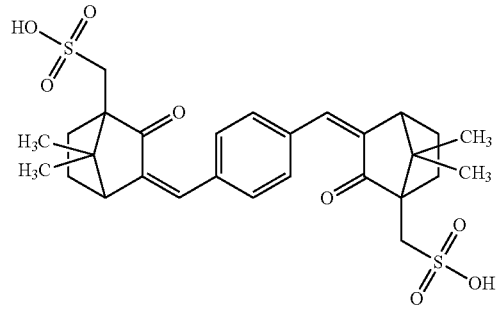 [SMILES: CC1(C)C2CCC1(CS(=O)(=O)O)C(=O)/C2=C\c1ccc(/C=C2\C(=O)C3(CS(=O)(=O)O)CCC2C3(C)C)cc1]

The composition may contain from about 0.001-20%, preferably 0.005-5%, more preferably about 0.005-3% by weight of the composition of UVA sunscreen. In the preferred embodiment of the invention the UVA sunscreen is Avobenzone, and it is present at not greater than about 3% by weight of the total composition.

B. UVB Chemical Sunscreens

The term "UVB sunscreen" means a compound that blocks UV radiation in the wavelength range of from about 290 to 320 nm. A variety of UVB chemical sunscreens exist including alpha-cyano-beta,beta-diphenyl acrylic acid esters as set forth in U.S. Pat. No. 3,215,724, which is hereby incorporated by reference in its entirety. One particular example of an alpha-cyano-beta,beta-diphenyl acrylic acid ester is Octocrylene, which is 2-ethylhexyl 2-cyano-3,3-diphenylacrylate. In certain cases the composition may contain no more than about 110% by weight of the total composition of octocrylene. Suitable amounts range from about 0.001-10% by weight Octocrylene may be purchased from BASF under the tradename Uvinul N-539.

Other suitable sunscreens include benzylidene camphor derivatives as set forth in U.S. Pat. No. 3,781,417, which is hereby incorporated by reference in its entirety. Such benzylidene camphor derivatives have the general formula:

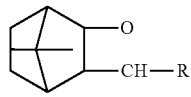

wherein R is p-tolyl or styryl, preferably styryl. Particularly preferred is 4-methylbenzylidene camphor, which is a lipid soluble UVB sunscreen compound sold under the tradename Eusolex 6300 by Merck. Also suitable are cinnamate derivatives having the general formula:

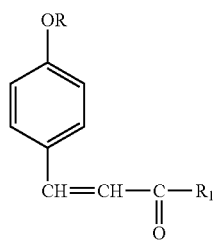

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol MCX, or BASF under the tradename Uvinul MC 80. Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at no more than about 3% by weight of the total composition.

Also suitable as UVB screening agents are various benzophenone derivatives having the general formula:

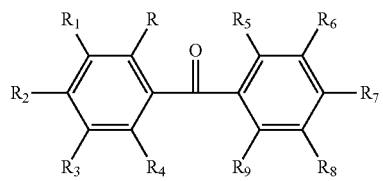

wherein R through $R_9$ are each independently H, OH, $NaO_3S$, $SO_3H$, $SO_3Na$, Cl, R", OR" where R" is $C_{1-20}$ straight or branched chain alkyl Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone), Benzophenone 4 (also referred to as Sulisobenzone), Benzophenone 5 (Sulisobenzone Sodium), and the like. Most preferred is Benzophenone 3.

Also suitable are certain menthyl salicylate derivatives having the general formula:

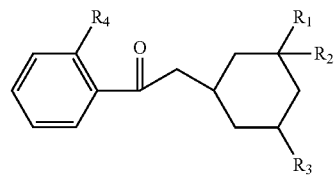

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and $R_4$ is hydroxyl or $NH_2$, the compound having the name homomethyl salicylate (also known as Homosalate) or menthyl anthranilate. Homosalate is available commercially from Merck under the tradename Eusolex HMS and menthyl anthranilate is commercially available from Haarmann & Reimer under the tradename Heliopan. If present, the Homosalate should be found at no more than about 15% by weight of the total composition.

Various amino benzoic acid derivatives are suitable UVB absorbers including those having the general formula:

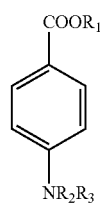

wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{1-8}$ straight or branched chain alkyl. Particularly preferred are PABA, ethyl hexyl dimethyl PABA (Padimate 0), ethyldihydroxypropyl PABA, and the like. If present Padimate 0 should be found at no more than about 8% by weight of the total composition. Salicylate derivatives are also acceptable UVB absorbers. Such compounds have the general formula:

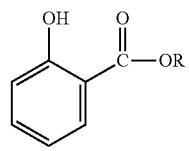

wherein R is a straight or branched chain alkyl, including derivatives of the above compound formed from mono-, di-, or triethanolamines. Particular preferred are octyl salicylate, TEA-salicylate, DEA-salicylate, and mixtures thereof.

Generally, the amount of the UVB chemical sunscreen present may range from about 0.001-45%, preferably 0.005-40%, more preferably about 0.01-35% by weight of the total composition.

If desired, the compositions of the invention may be formulated to have a certain SPF (sun protective factor) values ranging from about 1-50, preferably about 2-45, most preferably about 5-30. Calculation of SPF values is well known in the art.

It may be desirable to include one or more tyrosinase inhibiting agents in the compositions of the invention. Such tyrosinase inhibitors may include, but are not limited to, kojic acid, arbutin and hydroquinone. It may be desirable to include one or more further skin-lightening compounds in the compositions of the present invention. Suitable skin-lightening compounds include, but are not limited to, ascorbic acid and its derivatives, e.g., magnesium ascorbyl phosphate, ascorbyl glucosamine, ascorbyl palmitate. Other skin-lightening agents include adapalene, aloe extract, ammonium lactate, anethole derivatives, apple extract, azelaic acid, bamboo extract, bearberry extract, bletilla tuber, *Bupleurum falcatum* extract, burnet extract, butyl hydroxy anisole, butyl hydroxy toluene, deoxyarbutin, 1,3 diphenyl propane derivatives, 2,5 dihydroxybenzoic acid and its derivatives, 2-(4-acetoxyphenyl)-1,3 dithane, 2-(4-hydroxyphenyl)-1,3 dithane, ellagic acid, escinol, estragole derivatives, FADE OUT (available from Pentapharm), Fangfeng, fennel extract, *ganoderma* extract, gaoben, GATULINE WHITENING (available from Gattlefosse), genistic acid and its derivatives, glabridin and its derivatives, gluco pyranosyl-1-ascorbate, gluconic acid, glycolic acid, green tea extract, placenta extract, 4-Hydroxy-5-methyl-3[2H]-furanone, 4 hydroxyanisole and its derivatives, 4-hydroxy benzoic acid derivatives, hydroxycaprylic acid, inositol ascorbate, lactic acid, lemon extract, linoleic acid, MELA WHITE (available from Pentapharm), Morus alba extract, mulberry root extract, niacinamide, 5-octanoyl salicylic acid, parsley extract, *phellinus* linteus extract, pyrogallol derivatives, retinoic acid, retinol, retinol esters (acetate, propionate, palmitate, linoleate), 2,4 resorcinol derivatives, 3,5 resorcinol derivatives, rose fruit extract, salicylic acid, 3,4,5 trihydroxybenzyl derivatives, tranexamic acid, vitamin D3 and its analogs, and mixtures thereof.

It may be desirable to include one or more botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, *Padina pavonica* extract, *Thermus thermophilis* ferment extract, *Camelina sativa* seed oil, *Boswellia serrata* extract, olive extract, *Aribodopsis thaliana* extract, *Acacia dealbata* extract, *Acer saccharinum* (sugar maple), acidopholus, acorns, *aesculus, agaricus*, agave, agrimonia, algae, aloe, citrus, *brassica*, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza glabra, Salix nigra, Macrocycstis pyrifera, Pyrus malus, Saxifraga sarmentosa, Vitis vinifera, Morus nigra, Scutellaria baicalensis, Anthemis nobilis, Salvia sclarea, Rosmarinus officianalis, Citrus medica Limonum, Panax, Ginseng, Siegesbeckia orientalis, Fructus mume, Ascophyllum nodosum*, Bifida Ferment lysate, *Glycine soja* extract, *Beta vulgaris, Haberlea rhodopensis, Polygonum cuspidatum, Citrus Aurantium dulcis, Vitis vinifera, Selaginella tamariscina, Humulus lupulus, Citrus reticulata* Peel, *Punica granatum, Asparagopsis, Curcuma longa, Menyanthes trifoliata, Helianthus annuus, Hordeum vulgare, Cucumis sativus, Evernia prunastri, Evernia furfuracea*, and mixtures thereof.

It may also be desirable to incorporate one or more DNA repair enzymes into the composition of the invention. Suggested ranges are from about 0.00001 to about 35%, preferably from about 0.00005 to about 30%, more preferably from about 0.0001 to about 25% of one or more DNA repair enzymes. DNA repair enzymes useful in the compositions of the present invention are those described hereinabove.

In accordance with a further aspect of the present invention, cosmetic or dermatological compositions which stimulate healing or regenerative/rejuvenative properties in the skin, scalp and/or hair are provided. These compositions incorporate a material which emits NIR light, in a cosmetically or dermatologically acceptable vehicle. The NIR light-emitting materials employed may be any of the NIR light-emitting materials mentioned hereinabove. Healing, regenerative, and/or rejuvenative properties include, but are not limited to, anti-aging treatments, such as stimulating the production of collagen in skin, stimulating the production of elastin in skin, resurfacing the skin, such as by improving the texture of skin, reducing the size of pores in the skin, reducing the size and/or depth of wrinkles in the skin, and reducing the appearance of cellulite in the skin; stimulation of DNA synthesis and repair, reduction of inflammation in the skin; treatments for evening skin tone; treatment of acne; reduction in the appearance of acne scarring on the skin; stimulation of DNA synthesis and repair; rejuvenation of the hair and/or scalp, such as stimulating the growth phase of hair follicles, including dormant follicles, and reducing seborrhoiec inflammation.

According to a preferred embodiment of this aspect of the present invention, cosmetic or dermatological compositions which stimulate healing or regenerative/rejuvenative properties in the skin, scalp and/or hair contain the NIR light-emitting material in combination with at least one skin, scalp and/or hair benefit ingredient. The NIR light-emitting material and the skin, scalp and/or hair benefit ingredients may be any of those mentioned hereinabove. Skin, scalp and/or hair benefit ingredients may be any of those discussed hereinabove. Particularly preferred skin benefit agents are those which stimulate neocollagenesis or the production of elastin.

Any conventional packaging known for use with cosmetic products may be used to contain, distribute or mix compositions of the present invention. In the case where the formulations contain ingredients which may be incompatible during storage but which could be mixed at the time of use, or in the case that certain actives may be most efficacious when mixed with the NIR-light emitting material at the time of application, the use of a binary package consisting of two separate containers with associated separate nozzles or applicators is contemplated.

A still further aspect of the present invention concerns a substrate for incorporation into an article useful for stimulating a healing or regenerative/rejuvenative property in the skin, scalp and/or hair by transmitting NIR light to the skin, scalp and/or hair when the NIR light-emitting material is activated by exposure to UV or fluorescent light, and the substrate contacts, or is otherwise positioned in sufficient proximity to, the skin, scalp and/or hair to transmit the NIR light to the surface to be treated. The substrate is formed of a solid body and a NIR light-emitting material secured in or to the solid body. It will be understood that, because benefits are associated with proximity to the NIR light-emitting materials, direct contact with the skin, hair or scalp may not be necessary. NIR light-emitting materials useful in the substrates of the present invention include those described hereinabove. Materials useful in forming the solid substrate body are not particularly limited, provided that the NIR light-emitting material may be secured in or to the solid body by any known manufacturing method. Such materials may include, for example, plastics, metals, ceramics, and combinations thereof, as described hereinbelow.

The NIR light-emitting material may be secured in or to the solid body in particulate form or as part of a formulation containing the NIR light-emitting material, with or without additional skin, hair and/or scalp benefit agents, as described herein. The NIR light-emitting material may be embedded in the solid body, secured in or onto the body surface or a combination thereof. The NIR light-emitting material may also be coated or painted onto the surface of the solid body.

Materials useful in forming the substrate solid body include, but are not limited to, polymer/plastics, metals, ceramics, gels, foam structures, such as sponges, and organic materials such as plant (e.g., cotton, bamboo, Tampico, hemp) or animal fibers (e.g., wool). The substrates may take various forms, including, but not limited to, a sheet, a film, a fiber or a bristle, a textile or other product made from fiber or sheets, or any three-dimensional shape, such as a molded or extruded shape.

In accordance with one embodiment of the present invention, FIGS. 1a and 1b show a substrate 1 having a body 2 in the form a fiber or bristle 10. NIR light-emitting particles 20 are secured in or to the surface of fiber or bristle 10. In a further embodiment shown in FIGS. 2a and 2b, NIR light-emitting particles 20' are embedded in the fiber or bristle 30. NIR light-emitting particles 20 are also secured to or in a portion of the surface of fiber or bristle 30. In yet another embodiment of the invention shown in FIGS. 3a and 3b, substrate 60, in the form of a sheet, is provided with NIR light-emitting particles 20 secured to or in its surface. As further shown in FIGS. 4a and 4b, sheet 80 has NIR light-emitting particles 20' embedded throughout and NIR light-emitting particles 20 also secured to or in a portion of the sheet surface. Also contemplated is a fiber or a sheet in which NIR light-emitting particles 20' are embedded throughout, but are not provided on a surface of, the fiber or sheet.

At least one sheet substrate according to the present invention may be incorporated into a composite or multi-layered article comprising at least two layers of materials. Multi-layer substrates could have the NIR light-emitting material disposed on or in the surfaces directly contacting the skin, hair or scalp, on or in the surfaces opposite the contact surface, or layered between substrate surfaces. A combination of any of these configurations is also contemplated. The NIR light-emitting materials could be designed to be permanently affixed to the substrate body via adhesives, they could be present in a formula or delivery material on the surface of the substrate body that is not permanently attached, or the materials could be designed to weakly bond to the substrate body surface, but adapted to detach when contacted by a stronger force (i.e., attraction to the film and then dispersion or transfer to the contacting surface by applied intermolecular force/Van der Waals force on the substrate surface). Shown in FIG. 5 is an exploded view of composite article 110, including sheet 120 layered over sheet 130. NIR light-emitting particles 20 are secured to or in the upper surface of sheet 130. A composite article useful in the present invention need not be limited to two sheets of materials and each sheet may be formed of the same or different materials. Additionally, the sheet substrate may include NIR light-emitting particles 20, NIR light-emitting particles 20', or a combination thereof. The use of more than one NIR light-emitting material in or on the same substrate is also contemplated.

Figure 6:
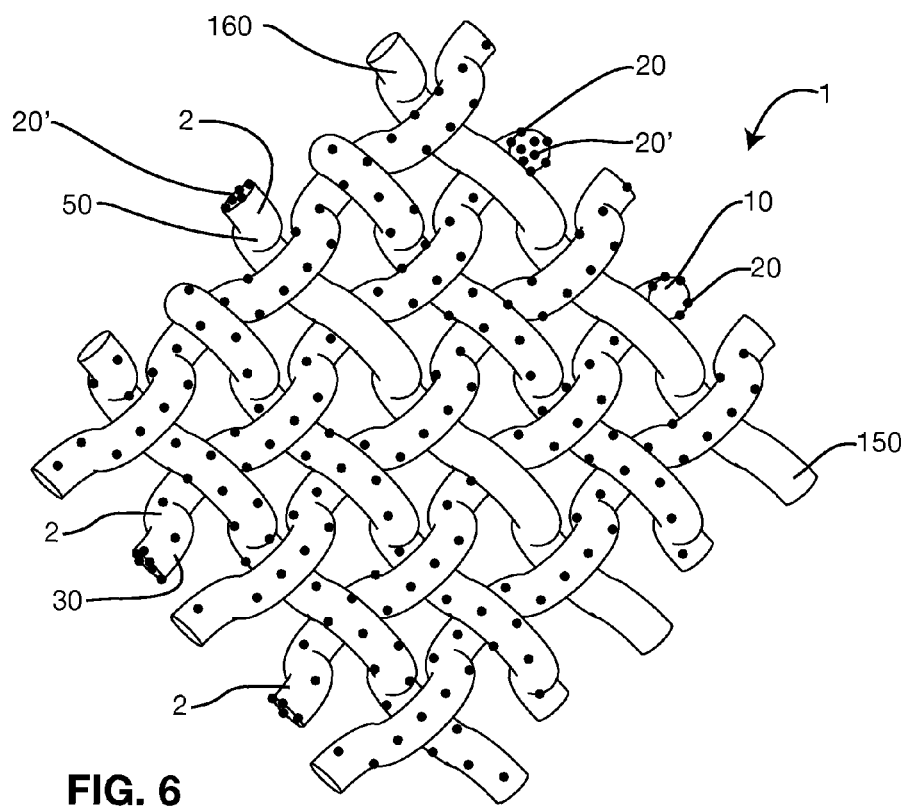
FIG. 6 is an illustration of a woven textile incorporating fibers according to the present invention.

Plastic or organic fibers or sheets may be utilized in woven textiles and nonwovens (e.g., fabrics that are bonded by chemicals, mechanically, thermally or with solvents) for use in patches, bandages, and so forth. As an example, fibers 10 and 30 are woven into textile material 150, shown in FIG. 6, together with fibers 50, which are embedded with NIR light-emitting particles but which include no surface particle treatment, and fibers 160 which do not incorporate any NIR light-emitting particles.

Fibers, sheets and textiles produced according to the present invention may be impregnated with cosmetic product, such as, but not limited to, a cosmetic treatment product, a foundation product, or a sun protection product. Optionally, such products could incorporate a NIR light-emitting material which is the same or different from the NIR light-emitting material in the fiber, sheet or textile.

Figure 7:
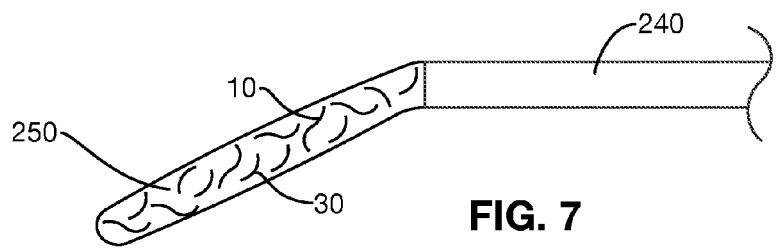
FIG. 7 is an illustration of a cosmetic applicator portion having a flocked tip end piece incorporating fibers according to the present invention.
Figure 8:
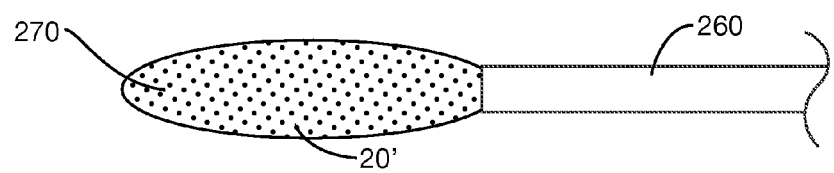
FIG. 8 is an illustration of another cosmetic applicator portion having a foam tip end piece incorporating embedded NIR light-emitting particles.
Figure 9:
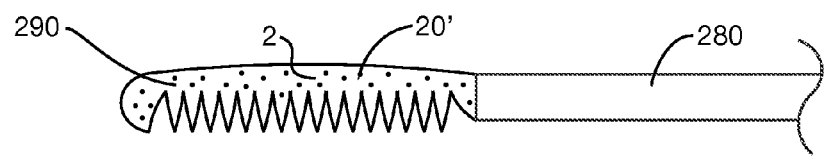
FIG. 9 is an illustration of a cosmetic applicator portion provided with a comb end piece containing embedded NIR light-emitting particles.
Figure 10:
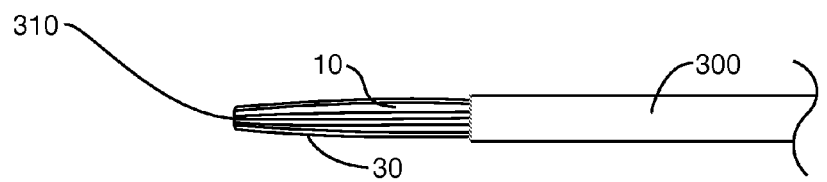
FIG. 10 is an illustration of a cosmetic applicator portion provided with a brush end piece incorporating bristles according to the present invention.
Figure 11:
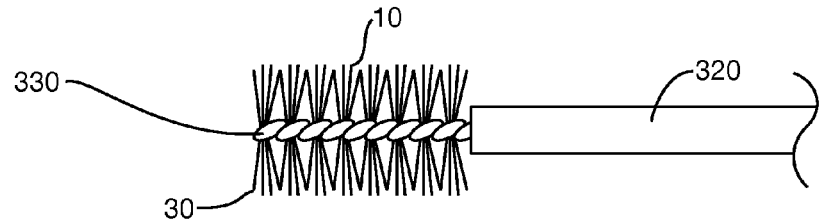
FIG. 11 is an illustration of another embodiment of a cosmetic applicator portion provided with a brush end piece incorporating bristles according to the present invention.
Figure 12:
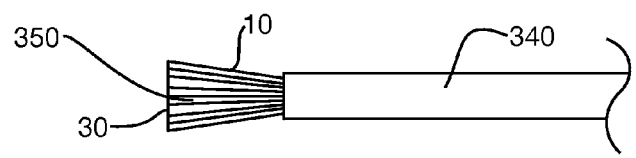
FIG. 12 is an illustration of another embodiment of a cosmetic applicator portion provided with a brush end piece incorporating bristles according to the present invention.

FIGS. 7-12 show various non-limiting embodiments of cosmetic applicator portions which incorporate substrates according to the present invention comprising NIR light-emitting particles which impart rejuvenating benefits to the skin, hair and/or the scalp. FIG. 7 illustrates a cosmetic applicator 240 having end piece 250 which may be formed of a flocked material made from a combination of fibers 10 and 30. A further cosmetic applicator 260, having foam end piece 270, incorporating NIR light-emitting particles 20', is shown in FIG. 8. Cosmetic applicator 280, shown in FIG. 9, includes comb end piece 290 formed with embedded NIR light-emitting particles 20'. The comb end piece may be formed from, for example, molded ceramic, molded plastic, cut from a plastics or metal sheet, and so forth. As a further example, FIG. 10 illustrates a brush applicator 300 having end piece 310 which is formed of a felt material made from fibers 10 and 30. The applicator may be used, for example, for applying a lip product or for lining the eyes. Brush 320, having mascara brush end piece 330, is shown in FIG. 11. The mascara brush is a twisted wire brush formed with bristles 10 and 30. A further example of a cosmetic applicator according to the present invention is brush 340 with end piece 350 formed from bristles 10 and 30. The brush may be used, for example, for the application of nail lacquer.

Plastic substrates useful in the present invention may be made by any known manufacturing process, and typically are made using extrusion and/or molding processes. Polymer material is blended with other materials having special properties, such as the NIR light-emitting particles, and additives, if desired, including, for example, performance fillers (e.g., glass, talc, nylon), release agents, colorants, and so forth, in a molten state, in a compounding process. A typical compounding process is described in U.S. Serial No. 2006/0174436 (to Brezler, published, Aug. 10, 2006), the disclosure of which is incorporated herein by reference in its entirety. The compounding process employs conventional plastic mixing processes (using specialized kneaders and twin mixing screws) to achieve the most homogenous state of the different raw materials included in the blend. Once mixed, the homogenous resin is extruded and then cut into pellets that may be used in, for example, injection molding, extrusion molding, or blow molding (i.e., injection or extrusion). After the plastic parts are molded in final, they will retain the homogenous quality of the compounded resin, including, in terms of the present invention, a desired quantity of NIR light-emitting particles distributed throughout the part.

The compounded resin, incorporating the NIR light-emitting material, may be extruded into sheets, tubes, rods and profiles, for example, solid or hollow profile ribbons, wires, fibers, filaments/bristles, or strands. A typical process for making filaments is described in U.S. Pat. No. 6,311,359 (to Brezler, issued Nov. 6, 2001), which is incorporated herein by reference in its entirety. The polymer resin pellets containing the NIR light emitting material are extruded through a spinneret to form filament strands which are quenched for solidification in cooling bath. The filaments are then subjected to a series of treatments which shape the filaments, improve their longitudinal strength and bend recovery prior to being cut. The filaments thus-produced may be grouped or twisted into brush forms, woven into fabrics or complex surfaces, or formed into nonwoven materials that resemble fabrics but are bound together by either chemicals, mechanical force, by use of heat, or by using adhesives/solvents. Fibers, bristles, filaments, or other strand materials (for example, nylon and/or polyester fibers) may be incorporated into brushes of varying kinds using techniques well known in the art.

The extrusion process can also yield single and multi-layered sheets, films, and bags by a process known as film casting. In this process, multiple sheets may be layered to produce films with excellent properties, including, but not limited to, barrier, aesthetic, or strength. Precise heating and cooling as well as mechanical techniques such as stretching these films can impart additional strength and molecular orientation to the product. The film casting process can yield one or more substrate surfaces bound together that could contain materials compounded with the NIR light-emitting particles. NIR light-emitting particles may also be placed on or between layers of substrates, which are held together by, for example, adhesives or solvents, heat bonding, or mechanical pressing. Some examples of film materials useful in the present invention including, but are not limited to, PP (Polypropylene), PVC (Polyvinyl Chloride), EVOH (Ethylene Vinyl Alcohol), PE (Polyethylene—High Density, Low Density or Linear Low Density types, for example). Non-polymer films which may be formed by n extrusion process may include, but are not limited to, those formed from paper pulp or aluminum foil. Preferably, the film would permit UV or fluorescent light to be transmitted to the NIR light-emitting material and would transmit NIR light from the NIR light-emitting material to a surface to be treated.

In the event that it is desired to use a substrate that permitted light to pass through it, the substrate also could take the form of a light filter. If precise permissive or exclusionary properties of light are needed, certain films, constructed to incorporate NIR light-emitting particles, could be used. This combination would permit NIR light transmission (i.e., NIR light passing filter) to the skin, scalp or hair, and at the same time, absorb other visible wavelengths. It would be appreciated that the film could also be layered over or otherwise adhered to a further substrate which is not itself impregnated with NIR light-emitting material.

Although a substrate may be reusable, it is also contemplated that a substrate in the form of a single use patch or mask, formed from any of the materials mentioned hereinabove and capable of being formed into a film or a sheet, may be used overnight and discarded after use.

Ceramics, certain plastics and/or metals also may be made into molded or formed shapes, useful in forming the substrates of the present invention, by means of a sintering process as part of a plastic injection molding process, a ceramic injection molding (CIM) process, a metal injection molding (MIM) process, or a powder injection molding (PIM) process. Such processes are well known, and generally involve combining powders of the ceramic, plastics or metal material with binders, and then fusing the materials together using pressure (such as, hot pressing or hot isostatic pressing) or without pressure (for example, by slip casting) after being heated to a temperature below the melting point of the material (also known as atomic diffusion). The product is molded, subjected to a binder removal process, and sintered to eliminate most of the pore volume formerly occupied by the binder. In accordance with the present invention, it is contemplated that the NIR light-emitting material could be mixed with the ceramic, plastic or metal powder, or could be incorporated into the binders, or could be infiltrated into the porous areas of a "green" or pre-sintered component. In the case in which the NIR light-emitting material is encapsulated, it is contemplated that the capsules could be fused together without adverse effect on the material.

Any three-dimensional shape or sheet of substrate of the present invention may also be formed from foam or sponge material made from, for example, Polyurethane (PU), Polyvinyl acetate (PVA), or Polyester (PE). In this process, polymer and other raw materials, including, NIR light-emitting material, are mixed (e.g., agitated) and heated in a pipe or confined area to cause a polymerization reaction. The polymer mixture is then combined with carbon dioxide as it is dispensed onto sheet like surfaces, causing it to expand. The sponge then resembles a large piece of rising dough which may be cut or ground to desired sizes. An example is a cellulose sponge made from cellulose fiber (e.g., wood pulp), other fibers, such as hemp for strength, and sodium sulphate crystals. The materials are combined in vats, poured into a mold and then heated. The holes in the sponge are created as the sodium sulphate melts and flows to the bottom of the mold and a final sponge product results.

NIR light-emitting particles may also be combined into coatings, paints, dyes and/or decorations which may then be used to coat the surface of any three-dimensional shape, sheet, bristle, fiber, film, and so forth, (i.e., solid body) for use as a substrate according to the present invention. The coating may be applied to the surface of the solid body by any means known in the art. As non-limiting examples, the coating may be sprayed onto a surface of the solid body, or the solid body could be dipped into the coating.

Figure 13:
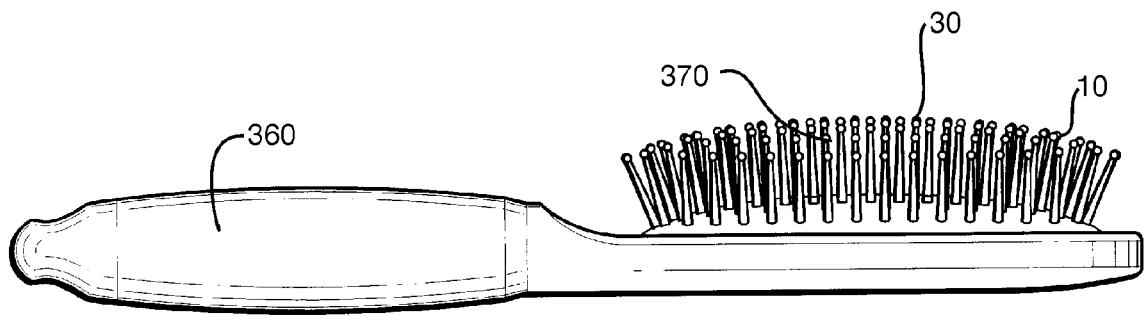
FIG. 13 is an illustration of a hair brush incorporating bristles according to the present invention.
Figure 14:
FIG. 14 is an illustration of a toothbrush incorporating bristles according to the present invention.

Any substrate according to the present invention may be adapted for use in any static applicator useful for treating the skin, hair or scalp. By "static applicator" it is meant that the applicator requires no batteries or motor for its operation. Such substrates, which may be provided in the form of, for example, a plurality of bristles or fibers, a foam structure, a ceramic structure, a metal form, a film, and so forth, may be incorporated into applicators of various types, including, but not limited to, a toothbrush, a hair brush, or a tool adapted for skin cleansing, for applying a treatment product (e.g., moisturizer, serum, sun protection product) or for applying a makeup product. As shown in FIG. 13, hairbrush 360 includes bristles 10 and 30 in bristle set 370. Toothbrush 380, shown in FIG. 14, includes tufts 390 formed from bristles 10 and 30.

Examples of packaging uses may be squeezable tubes, jars, caps, dip tubes, unit dose packages, or bottles, for possible formulations contained in these packages which can benefit from proximity to levels of NIR radiation. Clear packaging or packaging with layers that can be penetrated by ambient light or daylight may be desirable to "recharge" the NIR light-emitting particles over the life of the package. In the event that a formulation contains the NIR light-emitting particles, the clear packaging or packaging having layers that can be penetrated by ambient light or daylight may incorporate a different NIR light-emitting material for a synergistic benefit.

Also contemplated are kits containing products which incorporate substrates according to the present invention, such as a cosmetic formulation, a cosmetic patch or applicator, a combination thereof, and so forth, together with a light source for activating the NIR light-emitting particles. As non-limiting examples, mention may be made of a kit containing a cosmetic formulation, such as a foundation product, an applicator, and a UV light- or fluorescent light-emitting LED light source. The NIR light-emitting material in the foundation and/or the applicator, may be activated by exposing the foundation and/or the applicator, to the UV or fluorescent light prior to or after applying the foundation to the skin. Such a light source may also be provided in a kit with a cosmetic tool, such as a hairbrush, or the light source may be incorporated into the body of the tool per se.

A further aspect of the present invention concerns a method for stimulating healing or regenerative properties in the skin, scalp and/or hair which comprises applying to the skin, scalp or hair in need of such treatment a cosmetic or dermatological composition comprising a material which emits NIR light, in a cosmetically or dermatologically acceptable vehicle, and retaining the composition in contact with the skin and/or hair for a time sufficient to stimulate a healing or regenerative property to the skin, scalp and/or hair. The composition is exposed to UV or fluorescent light prior to, during, or after application of the composition to the skin, scalp and/or hair. Useful NIR light-emitting materials may be those described hereinabove.

A preferred embodiment of this aspect of the invention is a method for stimulating healing or regenerative properties in the skin, scalp and/or hair comprising applying to the skin, scalp and/or hair in need of such treatment a cosmetic or dermatological composition comprising a material which emits NIR light in combination with at least one skin, scalp and/or hair benefit agent, in a cosmetically or dermatologically acceptable vehicle, and retaining the composition in contact with the skin, scalp and/or hair for a time sufficient to stimulate a healing or regenerative property to the skin, scalp and/or hair. Healing or regenerative properties have been described hereinabove. Useful skin, scalp and/or hair benefit or therapeutic agents may be those mentioned hereinabove. The methods of the present invention are carried out in the absence of a NIR light-emitting laser or LED device.

Products for topical application to skin, scalp and/or hair, comprising a NIR light-emitting material, are adapted to be self-applied by the user without the need for one or multiple costly visits to a professional's office and without the need of an instrument or device to deliver NIR light. Additionally, while the NIR light is applied for a limited length of time in the professional's office, the NIR light-emitting material useful in the cosmetic compositions and methods of the present invention continues to emit NIR light and therefore prolongs the benefits of the skin or hair therapy for hours and even days longer than is possible as a result of the discrete periods of therapy applied by the professional. In contrast with laser therapy, for example, the luminescence emitted from the compositions of the present invention may occur throughout the day, and the night, in environments in which ambient or direct NIR light is minimal or absent. Moreover, the combination of the NIR-emitting material with a skin, scalp or hair benefit agent, e.g., a therapeutic active ingredient, is expected to improve and prolong the efficacy of treatment as compared with the use of the NIR light-emitting material or the therapeutic active when either is used alone. The effect of compositions of the present invention which combine a skin, scalp and/or hair therapeutic agent and a persistent NIR light-emitting material are expected to provide the most efficacious skin, scalp or hair treatment, since the NIR light-emitting effect could last for up to two weeks or longer, such as about 6 weeks, while the product remains in contact with the skin, scalp and/or hair.

Cosmetic and/or dermatological compositions of the invention, containing the NIR light-emitting material, with or without additional scalp, hair or skin benefit or active ingredients, and applied to the skin, scalp and/or hair, such as in the form of a facial cleanser, a shampoo, or a leave-in/leave-on treatment product for the scalp, hair or skin, such as a moisturizer or masque, and so forth, would typically remain in contact with the skin, scalp and/or hair for a period of time in the range of from about 1 minute to about 72 hours, including all times in-between those values, such as in the range of from about 1 hour to about 24 hours, until removed, such as by washing the skin, scalp and/or the hair. Nail lacquer may remain in contact with the nail for up to about 2 weeks, and may, for example, include active ingredients, in addition to the NIR light-emitting material, which benefit the nail bed and enhance nail growth.

It is also contemplated that compositions of the present invention may also include products incorporating NIR light-emitting material which remain in contact with the body for a period of up to 6 weeks or longer, such as hair dyes of all types, including temporary, semi-permanent and permanent, and any other hair treatment products, which may bind to, and remain associated with, the hair shaft for an extended period of time, providing continuous therapeutic effects to the hair and/or scalp. Such products may also contain additional active ingredients, as discussed hereinabove. It is further contemplated that the NIR light-emitting material and the active ingredient(s) would complement one another, so as to provide a synergistic benefit to the hair and/or scalp, such as provided as a result of increased penetration into the hair shaft of the active ingredient.

The methods of application of compositions of the present invention will depend on the ultimate intended use of the compositions. The compositions may be applied to the skin, hair or scalp on an as-needed basis, or according to a pre-set schedule. The compositions may be applied directly to clean skin, for example, before application of any moisturizer, foundation, make-up, etc. Alternatively, such compositions may be applied over moisturizer, and optionally over foundation and/or make-up. A composition according to the present invention is exposed to UV or fluorescent light, to activate the NIR light-emitting material, for a period of at least about one minute, before, during or after application of the composition to the skin, hair and/or scalp. The amount applied each time, the area of application, the duration of application, and the frequency of application can vary widely, depending on the specific need of the user. For example, the cosmetic compositions can be applied for a period of days to months or even years, and at a frequency ranging from about once or twice per day to about once per 1 to 6 weeks.

As one example, the compositions of the invention may be applied on a daily basis prior to sleep as part of a permanent skin care regimen. Specifically, the face is washed, and the composition is applied to skin immediately prior to bedtime. A composition of the present invention may, for example, be formulated as a night cream or a night repair or rejuvenating serum, which can be applied to the face of an individual before sleep without rinsing off. As a further example, a composition of the present invention may be formulated as an overnight facial or hair mask, which can be applied to the face or to the hair, respectively, before sleep, left thereon overnight, and then rinsed off the next morning. Once exposed to UV or fluorescent light to activate the NIR light-emitting material, the composition will persistently emit NIR light throughout the night and beyond, providing a continuous beneficial effect in the absence of any further excitation by UV or fluorescent light.

A further aspect of the present invention concerns a method for improving body composition, comprising applying to the skin of at least one body part containing fatty tissue and in need of such improvement, a cosmetic and/or dermatological composition comprising a NIR light-emitting material capable of providing thermal effects on fatty tissue, in a cosmetically or dermatologically acceptable vehicle, and retaining the composition in contact with the skin of the at least one body part while exercising the at least one body part for a time sufficient to generate the thermal effects of the NIR light on the fatty tissue to thereby increase lipolysis in the fatty tissue of the body part so as to boost fat reduction in the body part, wherein the composition is exposed to UV or fluorescent light prior to, during, or after application of the composition to the skin of the at least one body part.

In a preferred embodiment of this aspect of the invention, a cosmetic and/or dermatological composition comprising a NIR light-emitting material may further contain a cellulite reduction agent. Such ingredients include, but are not limited to, methylxanthines (e.g., caffeine, aminophylline and theophylline) which are also indicated in promoting lipolysis; and green tea extracts, e.g., EGCG.

While the present invention has been described hereinabove with reference to specific embodiments, features and aspects, it will be recognized that the invention is not thus limited, but rather extends in utility to other modifications, variations, applications, and embodiments, and accordingly all such other modifications, variations, applications, and embodiments are to be regarded as being within the spirit and scope of the present invention.

I claim:

1. A cosmetic or dermatological composition for topical application to skin, scalp and/or hair, comprising a near infrared (NIR) light-emitting material in a cosmetically or dermatologically acceptable vehicle, wherein the NIR light-emitting material is continually activated upon exposure to ambient light, day light, UV-light or fluorescent light emitting light source; and wherein the NIR light-emitting material is selected from phosphors of $MgSiO_3:Eu^{2+}$, $Dy^{3+}$, $Mn^{2+}$; $Ca_{0.2}Zn_{0.9}Mg_{0.9}Si_2O_6$, doped with $Eu^{+2}$, $Dy^{+3}$, $Mn^{2+}$; $SrAl_2O_4:Eu^{2+}$, $Dy^{3+}$, $Er^{3+}$; $La_3Ga_5Ge_3O_{14}:Cr^{3+}$, with or without co-dopants such as $Li^+$, $Zn^{2+}$, $Ca^{2+}$, $Mg^{2+}$ and $Dy^{3+}$; $Ln_3Ga_2Ge_4O_{14}:Cr^{3+}$ (Ln=Y, Gd, La or Lu); $LiGa_5O_8:Cr^{3+}$; $M_3Ga_2Ge_4O_{14}:Cr^{3+}$ (M=Sr or Ca); $La_3Ga_5SiO_{14}:Cr^{3+}$; $La_3Ga_{5.5}Nb^{0.5}O_{14}:Cr^{3+}$; $La_3Ga_5GeO_{14}:Cr^{3+}$; $Gd_3Ga_5O_{12}:Cr^{3+}$; and $Zn_xGa_yGe_zO_{(x+(3y/2)+2z)}:tCr^{3+}$, with or without co-dopants such as mR, where R is a co-dopant selected from a group consisting of alkaline earth ions, lanthanide ions and Li+ ions; x, y and z are integers from 1 to 5; t is 0.01 to 5 mol %; and m is 0 to 5 mol %; and combinations thereof; and wherein the NIR light-emitting material is present in the composition in amounts sufficient to achieve at least one of stimulating the production of collagen, stimulating the production of elastin, reducing the size of pores in the skin, reducing the size and/or depth of wrinkles in the skin, reducing the appearance of cellulite, reducing inflammation in the skin, evening the skin tone, treating ache, reducing the appearance of acne scarring, stimulating the growth cycle of hair follicles, reducing dandruff-causing seborrhea inflammation, and stimulating fatty tissue reduction after activation of the NIR light-emitting material.

2. The cosmetic or dermatological composition of claim 1, which persistently emits NIR light at least about 1 hour to about 6 weeks after exposure to ambient light, day light, UV-light or fluorescent light emitting light source.

3. The cosmetic or dermatological composition of claim 2, which persistently emits NIR light for a time of time of at least about 8 hours to about 2 weeks.

4. The cosmetic or dermatological composition of claim 1, wherein the activation of NIR light-emitting material proceeds over period of from about 1 minute to about 10 minutes.

5. The cosmetic or dermatological composition of claim 1, which is anhydrous, aqueous-based or solid.

6. The cosmetic or dermatological composition of claim 1, which is in the form of a solution, a serum, a gel, a cream, a lotion, a toner, a mousse, a spray, an ointment, an essence, a paste or a solid.

7. The cosmetic or dermatological composition of claim 1, wherein the NIR light-emitting material has a particle size in the range of from about 100 nanometers to about 100 micrometers.

8. The cosmetic or dermatological composition of claim 7, wherein the NIR light-emitting material has a particle size in the range of from about 500 nanometers to about 20 micrometers.

9. The cosmetic or dermatological composition of claim 1, wherein the NIR light-emitting material is present in the composition in an amount in the range of from about 0.001 wt. % to about 75 wt. %.

10. The cosmetic or dermatological composition of claim 1, comprising a cosmetic ingredient selected from the group consisting of oils, surfactants, film formers, pigments, powders and thickeners.

11. The cosmetic or dermatological composition of claim 1, comprising a cosmetic ingredient selected from the group consisting of moisturizers, humectants, botanical extracts, sunscreen agents, and DNA repair enzymes.

12. The cosmetic or dermatological composition of claim 1, in the form of a foundation, a blush, an eyeshadow a concealer, a lipgloss, a lip balm, a lipstick, a mascara, a shampoo, a hair conditioner, a facial or hair mask, a facial or hair serum, a hair styling lotion or balm, a hair dye, a sun care product, a nail lacquer, a depilatory, an exfoliant, or a facial or body moisturizer or treatment product.

* * * * *